United States Patent
Behar et al.

(10) Patent No.: US 10,478,065 B2
(45) Date of Patent: Nov. 19, 2019

(54) SYSTEMS AND METHODS FOR MONITORING SUBJECTS IN POTENTIAL PHYSIOLOGICAL DISTRESS

(71) Applicant: adidas AG, Herzogenaurach (DE)

(72) Inventors: Andrew Behar, Ojal, CA (US); Jeff Cobb, Ventura, CA (US); Alex Derchak, Summit, NJ (US); Barry Keenan, Sherman Oaks, CA (US); Dave Darnall, Huntington Beach, CA (US)

(73) Assignee: adidas AG, Herzogenaurach (DE)

( * ) Notice: Subject to any disclaimer, the term of this patent is extended or adjusted under 35 U.S.C. 154(b) by 300 days.

(21) Appl. No.: 15/333,655

(22) Filed: Oct. 25, 2016

(65) Prior Publication Data

US 2017/0296052 A1 Oct. 19, 2017

Related U.S. Application Data

(60) Division of application No. 11/503,350, filed on Aug. 10, 2006, now Pat. No. 9,492,084, which is a
(Continued)

(51) Int. Cl.
*A61B 5/00* (2006.01)
*G06F 19/00* (2018.01)
*G16H 80/00* (2018.01)

(52) U.S. Cl.
CPC .......... *A61B 5/0002* (2013.01); *A61B 5/4866* (2013.01); *A61B 5/4884* (2013.01);
(Continued)

(58) Field of Classification Search
CPC combination set(s) only.
See application file for complete search history.

(56) References Cited

U.S. PATENT DOCUMENTS 3,534,727 A 10/1970 Roman
3,731,184 A 5/1973 Goldberg et al.
(Continued)

FOREIGN PATENT DOCUMENTS

DE 4214263 A 11/1993
EP 0262778 A1 4/1988
(Continued)

OTHER PUBLICATIONS

6th Portuguese Conference on Biomedical Engineering,"BioEng' 2001 Conference Papers", (Jun. 2001) 6 pages.
(Continued)

*Primary Examiner* — William J Levicky
*Assistant Examiner* — Shirley X Jian
(74) *Attorney, Agent, or Firm* — Sterne, Kessler, Goldstein & Fox P.L.L.C.

(57) ABSTRACT

The present invention provides systems and methods for monitoring in real time the physiological status of one or more subjects, especially subject engaged in potentially hazardous or dangerous activities. Systems include wearable items with one or more physiological sensors and a local data unit (LDU) operatively coupled to the sensors. The LDUs digitize and filter sensor data, extract physiological parameters, determine abnormal or not acceptable physiological conditions, and communicate to external monitoring facilities. The external facilities display status and data concerning monitored subjects. In preferred embodiments, communication between the LDUs and the external monitoring facilities dynamically adjusts to the condition of the subjects and to system changes such as subjects and external facilities entering and leaving and/or moving from place to place. The invention also provides program products for performing this invention's methods.

18 Claims, 10 Drawing Sheets

Related U.S. Application Data continuation of application No. PCT/US2005/021433, filed on Jun. 17, 2005.

(60) Provisional application No. 60/580,971, filed on Jun. 18, 2004, provisional application No. 60/580,966, filed on Jun. 18, 2004.

(52) U.S. Cl.
CPC .......... *A61B 5/6804* (2013.01); *A61B 5/7264* (2013.01); *A61B 2560/0431* (2013.01); *G06F 19/3418* (2013.01); *G16H 80/00* (2018.01)

(56) References Cited

U.S. PATENT DOCUMENTS

| | | |
|---|---|---|
| 3,874,368 A | 4/1975 | Asrican |
| 3,926,177 A | 12/1975 | Hardway, Jr. et al. |
| 4,016,868 A | 4/1977 | Allison |
| 4,033,332 A | 7/1977 | Hardway, Jr. et al. |
| 4,102,331 A | 7/1978 | Grayzel et al. |
| 4,258,718 A | 3/1981 | Goldman |
| 4,267,845 A | 5/1981 | Robertson, Jr. et al. |
| 4,289,142 A | 9/1981 | Kearns |
| 4,306,567 A | 12/1981 | Krasner |
| 4,308,872 A | 1/1982 | Watson et al. |
| 4,373,534 A | 2/1983 | Watson et al. |
| 4,387,722 A | 6/1983 | Kearns |
| 4,433,693 A | 2/1984 | Hochstein |
| 4,446,872 A | 5/1984 | Marsoner et al. |
| 4,452,252 A | 6/1984 | Sackner |
| 4,456,015 A | 6/1984 | Sackner |
| 4,463,764 A | 8/1984 | Anderson et al. |
| 4,494,553 A | 1/1985 | Sciarra et al. |
| 4,537,196 A | 8/1985 | Phillipps et al. |
| 4,546,777 A | 10/1985 | Groch et al. |
| 4,548,204 A | 10/1985 | Groch et al. |
| 4,549,552 A | 10/1985 | Groch et al. |
| 4,572,197 A | 2/1986 | Moore et al. |
| 4,580,572 A | 4/1986 | Granek et al. |
| 4,648,407 A | 3/1987 | Sackner |
| 4,672,975 A | 6/1987 | Sirota |
| 4,753,088 A | 6/1988 | Harrison et al. |
| 4,777,962 A | 10/1988 | Watson et al. |
| 4,796,639 A | 1/1989 | Snow et al. |
| 4,800,495 A | 1/1989 | Smith |
| 4,807,640 A | 2/1989 | Watson et al. |
| 4,815,473 A | 3/1989 | Watson et al. |
| 4,817,625 A | 4/1989 | Miles |
| 4,819,752 A | 4/1989 | Zelin |
| 4,834,109 A | 5/1989 | Watson |
| 4,860,766 A | 8/1989 | Sackner |
| 4,863,265 A | 9/1989 | Flower et al. |
| 4,867,571 A | 9/1989 | Frick et al. |
| 4,911,167 A | 3/1990 | Corenman et al. |
| 4,920,969 A | 5/1990 | Suzuki et al. |
| 4,928,692 A | 5/1990 | Goodman et al. |
| 4,934,372 A | 6/1990 | Corenman et al. |
| 4,955,379 A | 9/1990 | Hall |
| 4,960,118 A | 10/1990 | Pennock |
| 4,966,155 A | 10/1990 | Jackson |
| 4,972,842 A | 11/1990 | Korten et al. |
| 4,981,139 A | 1/1991 | Pfohl |
| 4,986,277 A | 1/1991 | Sackner |
| 5,007,427 A | 4/1991 | Suzuki et al. |
| 5,025,791 A | 6/1991 | Niwa |
| 5,036,857 A | 8/1991 | Semmlow et al. |
| 5,040,540 A | 8/1991 | Sackner |
| 5,074,129 A | 12/1991 | Matthew |
| 5,076,801 A | 12/1991 | Schroll |
| 5,099,841 A | 3/1992 | Heinonen et al. |
| 5,099,855 A | 3/1992 | Yount |
| 5,111,817 A | 5/1992 | Clark et al. |
| 5,131,399 A | 7/1992 | Sciarra |
| 5,143,089 A | 9/1992 | Alt |
| 5,159,935 A | 11/1992 | Sackner et al. |
| 5,173,151 A | 12/1992 | Namose |
| 5,178,151 A | 1/1993 | Sackner |
| 5,224,479 A | 7/1993 | Sekine |
| 5,228,449 A | 7/1993 | Christ et al. |
| 5,241,300 A | 8/1993 | Buschmann |
| 5,271,551 A | 12/1993 | Roepke |
| 5,299,120 A | 3/1994 | Kaestle |
| 5,301,678 A | 4/1994 | Watson et al. |
| 5,329,932 A | 7/1994 | Yount |
| 5,331,968 A | 7/1994 | Williams et al. |
| 5,333,106 A | 7/1994 | Lanpher et al. |
| 5,348,008 A | 9/1994 | Bornn et al. |
| 5,353,793 A | 10/1994 | Bornn et al. |
| 5,416,961 A | 5/1995 | Vinay |
| 5,447,164 A | 9/1995 | Shaya et al. |
| RE35,122 E | 12/1995 | Corenman et al. |
| 5,520,192 A | 5/1996 | Kitney et al. |
| 5,533,511 A | 7/1996 | Kaspari et al. |
| 5,535,738 A | 7/1996 | Estes et al. |
| 5,544,661 A | 8/1996 | Davies et al. |
| 5,564,429 A | 10/1996 | Bornn et al. |
| 5,577,510 A | 11/1996 | Chittum et al. |
| 5,582,337 A | 12/1996 | McPherson et al. |
| 5,584,295 A | 12/1996 | Muller et al. |
| 5,588,425 A | 12/1996 | Sackner et al. |
| 5,601,088 A | 2/1997 | Swanson et al. |
| 5,611,085 A | 3/1997 | Rasmussen |
| 5,617,847 A | 4/1997 | Howe |
| 5,694,939 A | 12/1997 | Cowlings |
| 5,718,234 A | 2/1998 | Warden et al. |
| 5,719,950 A | 2/1998 | Ostin et al. |
| 5,720,709 A | 2/1998 | Schnall |
| 5,724,025 A | 3/1998 | Tavori |
| 5,749,365 A | 5/1998 | Magill |
| 5,820,567 A | 10/1998 | Mackie |
| 5,825,293 A | 10/1998 | Ahmed et al. |
| 5,848,027 A | 12/1998 | Dotter |
| 5,882,307 A | 3/1999 | Wright et al. |
| 5,890,054 A * | 3/1999 | Logsdon ............... H04W 76/50 455/11.1 |
| 5,899,855 A | 5/1999 | Brown |
| 5,913,830 A | 6/1999 | Miles |
| 5,921,920 A | 7/1999 | Marshall et al. |
| 5,937,854 A | 8/1999 | Stenzler |
| 5,989,193 A | 11/1999 | Sullivan |
| 5,991,922 A | 11/1999 | Banks |
| 6,002,952 A | 12/1999 | Diab et al. |
| 6,015,388 A | 1/2000 | Sackner et al. |
| 6,018,677 A | 1/2000 | Vidrine et al. |
| 6,035,154 A | 3/2000 | Takahata et al. |
| 6,047,203 A | 4/2000 | Sackner et al. |
| 6,066,093 A | 5/2000 | Kelly et al. |
| 6,067,462 A | 5/2000 | Diab et al. |
| 6,068,568 A | 5/2000 | Kozakura et al. |
| 6,070,098 A | 5/2000 | Moore-Ede et al. |
| 6,120,441 A | 9/2000 | Griebel |
| 6,142,953 A | 11/2000 | Burton et al. |
| 6,145,551 A | 11/2000 | Jayaraman et al. |
| 6,157,871 A * | 12/2000 | Terranova ............... B67D 7/067 700/231 |
| 6,198,394 B1 | 3/2001 | Jacobsen et al. |
| 6,223,072 B1 | 4/2001 | Mika et al. |
| 6,254,551 B1 | 7/2001 | Varis |
| 6,261,238 B1 | 7/2001 | Gravely |
| 6,273,859 B1 | 8/2001 | Remmers et al. |
| 6,278,999 B1 | 8/2001 | Knapp |
| 6,287,264 B1 | 9/2001 | Hoffman |
| 6,302,844 B1 | 10/2001 | Walker et al. |
| 6,306,088 B1 | 10/2001 | Krausman et al. |
| 6,341,504 B1 | 1/2002 | Istook |
| 6,361,501 B1 | 3/2002 | Amano et al. |
| 6,381,482 B1 | 4/2002 | Jayaraman et al. |
| 6,413,225 B1 | 7/2002 | Sackner et al. |
| 6,436,057 B1 | 8/2002 | Goldsmith |
| 6,443,890 B1 | 9/2002 | Schulze et al. |
| 6,449,504 B1 | 9/2002 | Conley et al. |
| 6,450,955 B1 * | 9/2002 | Brown ................ A61B 5/0002 600/300 |

(56) References Cited

U.S. PATENT DOCUMENTS

| | | |
|---|---|---|
| 6,454,719 B1 | 9/2002 | Greenhut |
| 6,461,307 B1 | 10/2002 | Kristbjarnarson et al. |
| 6,463,385 B1 | 10/2002 | Fry |
| 6,478,736 B1 | 11/2002 | Mault |
| 6,483,929 B1 | 11/2002 | Murakami et al. |
| 6,485,431 B1 | 11/2002 | Campbell |
| 6,506,153 B1 | 1/2003 | Littek et al. |
| 6,511,424 B1 | 1/2003 | Moore-Ede et al. |
| 6,513,532 B2 | 2/2003 | Mault et al. |
| 6,551,252 B2 | 4/2003 | Sackner et al. |
| 6,579,231 B1 | 6/2003 | Phipps |
| 6,604,115 B1 | 8/2003 | Gary et al. |
| 6,633,772 B2 | 10/2003 | Ford et al. |
| 6,647,252 B2 | 11/2003 | Smith et al. |
| 6,656,127 B1 | 12/2003 | Ben-Oren et al. |
| 6,687,523 B1 | 2/2004 | Jayaraman et al. |
| 6,699,194 B1 | 3/2004 | Diab et al. |
| 6,702,752 B2 | 3/2004 | Dekker |
| 6,709,402 B2 | 3/2004 | Dekker |
| 6,721,594 B2 | 4/2004 | Conley et al. |
| 6,723,055 B2 | 4/2004 | Hoffman et al. |
| 6,726,636 B2 | 4/2004 | Der Ghazarian et al. |
| 6,727,197 B1 | 4/2004 | Wilson et al. |
| 6,747,561 B1 | 6/2004 | Reeves |
| 6,755,795 B2 | 6/2004 | Marmaropoulos et al. |
| 6,775,389 B2 | 8/2004 | Harrison et al. |
| 6,783,498 B2 | 8/2004 | Sackner et al. |
| 6,801,916 B2 | 10/2004 | Roberge et al. |
| 6,817,979 B2 | 11/2004 | Nihtila |
| 6,858,006 B2 | 2/2005 | MacCarter et al. |
| 6,881,192 B1 | 4/2005 | Park |
| 6,941,775 B2 | 9/2005 | Sharma |
| 6,955,647 B2 | 10/2005 | Rice |
| 6,961,448 B2 | 11/2005 | Nichols et al. |
| 6,970,731 B1 | 11/2005 | Jayaramen et al. |
| 6,993,378 B2 | 1/2006 | Wiederhold et al. |
| 7,001,337 B2 | 2/2006 | Dekker |
| 7,073,129 B1 | 7/2006 | Robarts et al. |
| 7,077,810 B2 | 7/2006 | Lange et al. |
| 7,081,095 B2 | 7/2006 | Lynn et al. |
| 7,082,327 B2 | 7/2006 | Houben |
| 7,099,714 B2 | 8/2006 | Houben |
| 7,104,962 B2 | 9/2006 | Lomask et al. |
| 7,110,554 B2 | 9/2006 | Brennan et al. |
| 7,154,398 B2 | 12/2006 | Chen et al. |
| 7,174,277 B2 | 2/2007 | Vock et al. |
| 7,207,948 B2 | 4/2007 | Coyle |
| 7,211,053 B2 | 5/2007 | Marmaropoulos et al. |
| 7,254,516 B2 | 8/2007 | Case et al. |
| 7,267,652 B2 | 9/2007 | Coyle et al. |
| 7,319,385 B2 | 1/2008 | Ruha |
| 7,604,603 B2 | 10/2009 | Sackner et al. |
| 7,670,295 B2 | 3/2010 | Sackner et al. |
| 7,727,161 B2 | 6/2010 | Coyle et al. |
| 7,762,953 B2 | 7/2010 | Derchak et al. |
| 7,809,433 B2 | 10/2010 | Keenan |
| 7,811,231 B2 * | 10/2010 | Jin ................. A61B 5/0002 600/300 |
| 7,878,979 B2 | 2/2011 | Derchak |
| 8,475,371 B2 | 7/2013 | Derchak et al. |
| 8,628,480 B2 | 1/2014 | Derchak |
| 8,971,936 B2 | 3/2015 | Derchak |
| 9,326,705 B2 | 5/2016 | Derchak |
| 9,462,975 B2 | 10/2016 | Sackner et al. |
| 9,526,419 B2 | 12/2016 | Derchak et al. |
| 9,545,222 B2 | 1/2017 | Derchak et al. |
| 9,750,429 B1 | 9/2017 | Sackner et al. |
| 2002/0032386 A1 | 3/2002 | Sackner et al. |
| 2002/0084130 A1 | 7/2002 | Der Ghazarian et al. |
| 2002/0090667 A1 | 7/2002 | Ratcliffe et al. |
| 2002/0123701 A1 | 9/2002 | Eriksen et al. |
| 2003/0004403 A1 | 1/2003 | Drinan et al. |
| 2003/0064718 A1 * | 4/2003 | Haines ................. H04W 48/16 455/423 |
| 2003/0065536 A1 * | 4/2003 | Hansen ............. A61B 5/14532 705/2 |
| 2003/0100843 A1 | 5/2003 | Hoffman |
| 2003/0135097 A1 | 7/2003 | Wiederhold et al. |
| 2003/0135127 A1 | 7/2003 | Sackner et al. |
| 2003/0163287 A1 | 8/2003 | Vock et al. |
| 2003/0185408 A1 | 10/2003 | Causevic et al. |
| 2003/0187341 A1 | 10/2003 | Sackner et al. |
| 2003/0226695 A1 | 12/2003 | Mault et al. |
| 2003/0233031 A1 | 12/2003 | Rice |
| 2004/0010420 A1 | 1/2004 | Rooks |
| 2004/0019289 A1 | 1/2004 | Ross |
| 2004/0030224 A1 | 2/2004 | Sotos et al. |
| 2004/0059205 A1 | 3/2004 | Carlson et al. |
| 2004/0092801 A1 | 5/2004 | Drakilic |
| 2004/0111040 A1 | 6/2004 | Ni et al. |
| 2004/0117204 A1 | 6/2004 | Mazar et al. |
| 2004/0122334 A1 | 6/2004 | Yamashiro |
| 2004/0143194 A1 | 7/2004 | Kihara et al. |
| 2004/0186365 A1 * | 9/2004 | Jin ................. A61B 5/0002 600/365 |
| 2004/0204636 A1 | 10/2004 | Diab et al. |
| 2004/0210147 A1 | 10/2004 | Houben |
| 2004/0225227 A1 | 11/2004 | Newman |
| 2004/0249299 A1 | 12/2004 | Cobb |
| 2005/0027207 A1 | 2/2005 | Westbrook et al. |
| 2005/0054941 A1 | 3/2005 | Ting et al. |
| 2005/0076908 A1 | 4/2005 | Lee et al. |
| 2005/0080566 A1 | 4/2005 | Vock et al. |
| 2005/0119586 A1 | 6/2005 | Coyle et al. |
| 2005/0125970 A1 | 6/2005 | Nolan |
| 2005/0211247 A1 | 9/2005 | Noda et al. |
| 2005/0228234 A1 | 10/2005 | Yang |
| 2005/0240087 A1 | 10/2005 | Keenan et al. |
| 2005/0256385 A1 | 11/2005 | Diab et al. |
| 2006/0000420 A1 | 1/2006 | Davies et al. |
| 2006/0036183 A1 | 2/2006 | Sackner et al. |
| 2006/0041200 A1 | 2/2006 | Dotter et al. |
| 2006/0074334 A1 | 4/2006 | Coyle |
| 2006/0122528 A1 | 6/2006 | Gal |
| 2006/0178591 A1 | 8/2006 | Hempfling |
| 2006/0258914 A1 | 11/2006 | Derchak et al. |
| 2006/0293609 A1 | 12/2006 | Stahmann et al. |
| 2007/0027368 A1 | 2/2007 | Collins et al. |
| 2007/0049843 A1 | 3/2007 | Derchak |
| 2007/0050715 A1 | 3/2007 | Behar |
| 2007/0094045 A1 * | 4/2007 | Cobbs ................. G16H 40/20 705/2 |
| 2007/0094046 A1 * | 4/2007 | Cobbs ................. G16H 40/20 705/2 |
| 2007/0105083 A1 | 5/2007 | Riener et al. |
| 2007/0150006 A1 | 6/2007 | Libbus et al. |
| 2007/0177770 A1 | 8/2007 | Derchak et al. |
| 2007/0208262 A1 | 9/2007 | Kovacs |
| 2007/0209669 A1 | 9/2007 | Derchak |
| 2007/0270671 A1 | 11/2007 | Gal |
| 2007/0293781 A1 | 12/2007 | Sims et al. |
| 2008/0015454 A1 | 1/2008 | Gal |
| 2008/0027341 A1 | 1/2008 | Sackner |
| 2008/0045815 A1 | 2/2008 | Derchak et al. |
| 2008/0051667 A1 | 2/2008 | Goldreich |
| 2008/0051839 A1 | 2/2008 | Libbus et al. |
| 2008/0082018 A1 | 4/2008 | Sackner et al. |
| 2008/0184878 A1 | 8/2008 | Chen et al. |
| 2008/0221401 A1 | 9/2008 | Derchak et al. |
| 2008/0269644 A1 | 10/2008 | Ray |
| 2009/0131759 A1 | 5/2009 | Sims et al. |
| 2010/0274100 A1 | 10/2010 | Behar et al. |
| 2011/0009766 A1 | 1/2011 | McCool |
| 2011/0050216 A1 | 3/2011 | Stone |
| 2011/0054289 A1 | 3/2011 | Derchak et al. |
| 2011/0054290 A1 | 3/2011 | Derchak |

FOREIGN PATENT DOCUMENTS

| | | |
|---|---|---|
| EP | 0875199 A1 | 4/1998 |
| EP | 0 846 440 A2 | 6/1998 |
| GB | 1596298 A | 8/1981 |

(56) References Cited

FOREIGN PATENT DOCUMENTS

| | | |
|---|---|---|
| GB | 2116725 A | 9/1983 |
| JP | 53126786 A | 6/1978 |
| JP | 58109031 A | 6/1983 |
| JP | H0-637933 A | 12/1988 |
| JP | 1091834 A | 4/1989 |
| JP | H0-5168602 A | 7/1993 |
| JP | H0-5298589 A | 11/1993 |
| JP | H0-7227383 A | 8/1995 |
| JP | H08-510399 A | 11/1996 |
| JP | 2001-516253 A | 9/1998 |
| JP | H10-295652 A | 11/1998 |
| JP | 2001-104259 A | 4/2001 |
| JP | 2004-160051 A | 6/2004 |
| WO | WO 95/16393 A1 | 6/1995 |
| WO | WO 98/010699 A1 | 3/1998 |
| WO | WO 01/028420 A1 | 4/2001 |
| WO | WO 2001/76467 A2 | 10/2001 |
| WO | WO 2002/060370 A2 | 8/2002 |
| WO | WO 2002/069878 A1 | 12/2002 |
| WO | WO 2003/022149 A2 | 3/2003 |
| WO | WO 2004/019503 A2 | 3/2004 |
| WO | WO 2004/026126 A1 | 4/2004 |
| WO | WO 2004/045407 A1 | 6/2004 |
| WO | WO 2005/115242 A2 | 12/2005 |
| WO | WO 2006/002338 A2 | 1/2006 |
| WO | WO 2006/009830 A2 | 1/2006 |
| WO | WO 2007/021645 A2 | 2/2007 |
| WO | WO 2007/069111 A2 | 6/2007 |
| WO | WO 2007/089751 A2 | 8/2007 |
| WO | WO 2009/074973 A1 | 6/2009 |
| WO | WO 2010/027515 A1 | 3/2010 |

OTHER PUBLICATIONS

Aliverti, A. et al., "Chronic Obstructive Pulmonary Disease: Regional Chest Wall Volumes During Exercise in Chronic Obstructive Pulmonary Disease." Thorax, 59:210-216, 7 pages, 2004.
Almeida et al., "Wavelet Transform Based Matlab System for the Detection and Delineation of QRS Complexes in Ambulatory ECG Recordingd", 6th Portuguese Conference on Biomedical Engineering (Jun. 2001), 2 pages.
Anderer et al., "Artifact Processing in Computerized Analysis of Sleep EEG—A Review" Neuropsychobiology, 40:150-157 (1999), 8 pages.
Bianchi et al., "Extraction of the Respiration Influence From the Heart Rate Variability Signal by Means of Lattice Adaptive Filter", IEEE Transactions on Biomedical Engineering, pp. 121-122 (1994), 2 pages.
National Biometric Test Center, "The Functions of Biometric Identification Devices", San Jose State University Biometrics Publications, www.engr.sjsu.edu/biometrics/publications_tech.html (printed Jul. 28, 2005), 25 pages.
National Biometric Test Center, "Biometric Technology—Testing, Evaluation, Results", San Jose State University Biometrics Publications, www.engr.sjsu.edu/biometrics/publications_tech.html (printed Jul. 28, 2005), 13 pages.
Blechert et al., "Identifying Anxiety States Using Broad Sampling and Advance Processing of Peripheral Physiological Information," Psychosom Med Dec. 2007;69(9):935-43 Epub Nov. 8, 2007, 6 pages.
Bloch et al., "Specific respiratory patterns distinguish among human basic emotions," International Journal of Psychophysiology, 11:141-154 (1991), 14 pages.
Bonnet et al., "EEG Arousals: Scoring Rules and Examples, A Preliminary Report from the Sleep Disorders Atlas Task Force of the American Sleep Disorders Association," Sleep, 152(2): 173-184 (1992), 12 pages.
Brach "Cheyne-Stokes respiration in patients with congestive heart failure," Swiss Med Weekly 133:605-610 (2003), 7 pages.
Costa et al., "Multiscale Entropy Analysis of Complex Physiologic Time Series," Physical Review Letters 89(6):068102-1-4 Aug. 5, 2002, 4 pages.
Coyle et al., "Home Measurement of Cough Indicates Circadian Frequency Pattern and Abnormal Distribution During Sleep," LifeShirt System, study sponsored by Pfizer, Inc., Jun. 2004, 1 page.
Gore Electronic Products, "Expanded PTFE Insulation Material", www.goreelectronics.com (visited Aug. 2005), 4 pages.
Grossman et al., "Reliability of Respiratory Tidal Volume Estimation by Means of Ambulatory Inductive Plethysmography," Biomed Sci Instrum 42:193-8 (2006), 6 pages.
Grossman et al., "A Comparison of Three Quantification Methods for Estimation of Respiratory Sinus Arrhythmia", Psychophycology, 27(6):702-714 (1990), 17 pages.
Istepanian et al., "Microcontroller-Based Underwater Acoustic ECG Telemetry System", IEEE Transactions on Information Technology in Biomedicine, 1(2):150-154 (Jun. 1997), 5 pages.
Keenan et al., "Adaptive Filtering of Heart Rate Signals for an Improved Measure of Sympathovagal Balance," Jan. 1, 2005, 8 pages.
Klabunde, "Electrocardiogram (EKG, ECG)", Cardiovascular Physiology Concepts, www.cvphysiology.com (visited Mar. 2005), 3 pages.
Lake et al., "Sample entropy analysis of neonatal heart rate variability," Am J Physiol Regul Integr Comp 283:R789-97 (2002), 10 pages.
Marin et al., "Inspiratory Capacity, Dynamic Hyperinflation, Breathlessness, and Exercise Performance During the 6-Minute-Walk Test in Chronic Obstructive Pulmonary Disease", Am. J. Respir. Crit. Care Med., vol. 163., pp. 1395-1399, (2001), 5 pages.
McCool et al., "Estimates of ventilation from body surface measurements in unstricted subjects," J. Appl. Physiol. 61(3):1114-9 (1986), 6 pages.
McCool et al., "Tidal Volume and Respiratory Timing Derived From a Portable Ventilation Monitor," Chest 122:684-91 (2002), 10 pages.
McNaughton et al., "Metallized Polymer Fibers as Leadwires and Intrafascicular Microelectrodes", J. Neurosci. Methods, 70(1):103-10 (1996), 2 pages.
Micro-Coax, "About Micro-Coax", www.micro-coax.com (visited Aug. 2004), 9 pages.
Niskanen et al., "Software for Advanced HRV Analysis", University of Kuopio Department of Applied Physics Report Series, pp. 1-11 (Feb. 2002), 12 pages.
O'Donnell, "Ventilatory Limitations in Chronic Obstructive Pulmonary Disease", Medicine & Science in Sports & Exercise, pp. 5647-S655, (2001), 9 pages.
O'Donnell et al., "Dynamic Hyperinflation and Exercise Intolerance in Chronic Obstructive Pulmonary Disease", Am. J. Respir. Crit. Care Med., 164:770-777 (2001), 8 pages.
Park et al., "Automated Detection and Elimination of Periodic ECG Artifacts in EEG Using the Energy Interval Histogram Method", IEEE Transactions on Biomedical Engineering 49(12):1526-1533 (2002), 8 pages.
Pietraszek et al., "Simple Telemetry System for ECG Recording", Polish J. Med. Phys. & Eng. 2002; 8(3): 193-198, 4 pages.
Rampil, "A Primer for EEG Signal Processing in Anesthesia," Anesthesiology 89(4):980-1002 Oct. 1998, 15 pages.
Richman et al., "Physiological time-series analysis using approximate entropy and sample entropy," Am J. Physiol Circ Physiol 278:H2039-49 (2000), 11 pages.
Signal Consulting Inc., "Inductance of Circular Loop", www.sigcon.com (visited Aug. 2005), 2 pages.
Sijbers et al., "Reduction of ECG and gradient related arifacts in simultaneously recorded human EEG/MRI data," Magnetic Resonance Imaging 18:881-6 (2000), 6 pages.
Snyder et al., "Ventilatory Responses to Hypoxia and High Altitude During Sleep in Aconcagua Climbers," Wilderness and Environmental Medicine 18:138-145 (2007), 8 pages.
Szabo et al., "Prognostic Value of Heart Rate Variability in Chronic Congestive Heart Failure Secondary to Idiopathic or Ischemic Dilated Cardiomypathy," Am J Cardiol. 79:978-980 (1997), 3 pages.

(56) References Cited

OTHER PUBLICATIONS van Dijk et al., "Determinants of Brachial Artery mean 24 h PulsePressure in Individuals with Type II diabetes mellitus and untreated mild hypertension", Clinical Science (2002), 102, pp. 177-186, 10 pages.
Vogiatzis, et al., "Respiratory Kinematics by Optoelectronic Plethysmography During Exercise in Men and Women.", Eur J of App Physiol, 581-587, 7 pages, 2004, 7 pages.
Wilhelm et al., "Distinguishing Emotional From Physical Activation in Ambulatory Psychophysiological Monitoring," Biomed Sci Instrum 42:458-63 (2006), 6 pages.
Wachowski, Andy and Larry, The Matrix, released Mar. 31, 1999 by Warner Bros. Pictures, see 1:26:29, 2:03:10, and 2:04:41, 13 pages.
Wilhelm et al., "Taking the laboratory to the skies: Ambulatory assessment of self-report, autonomic, and respiratory responses in flying phobia," Psychophysiology 35:596-606 (1998), 11 pages.
International Search Report and the Written Opinion of the International Searching Authority, application No. PCT/US06/60264, dated Jan. 15, 2008, 8 pages.
International Search Report and the Written Opinion of the International Searching Authority, application No. PCT/US2007/82688, dated May 8, 2008, 7 pages.
International Search Report and the Written Opinion of the International Searching Authority, application No. PCT/US2008/072414, dated Nov. 12, 2008, 7 pages.
International Search Report and the Written Opinion of the International Searching Authority, application No. PCT/US2008/061171, dated Nov. 14, 2008, 10 pages.
Supplementary Partial European Search Report of the European Patent Office, Application No. EP 06784447.2, dated Jan. 20, 2010, 9 pages.
Extended European Search Report for Application No. EP 07798146.2, Applicant: adidas AG, dated Oct. 19, 2010.
Extended European Search Report for Application No. EP 10174873.9, Applicant: adidas AG, dated Dec. 8, 2010.
Extended European Search Report for Application No. EP 10174680.8, Applicant: adidas AG, dated Dec. 9, 2010.
Extended European Search Report for Application No. EP 10174876.2, Applicant: adidas AG, dated Dec. 9, 2010.
Extended European Search Report for Application No. EP 10174881.2, Applicant: adidas AG, dated Dec. 9, 2010.
Extended European Search Report for Application No. EP 10174683.2, Applicant: adidas AG, dated Dec. 27, 2010.
Partial European Search Report for Application No. EP 10174885.3, Applicant: adidas AG, dated Jan. 4, 2011.
Office Action dated Aug. 2, 2010 from U.S. Appl. No. 11/373,822, Sackner, System and Methods for Ambulatory Monitoring of Physiological Signs, filed Mar. 9, 2006.
Office Action dated Sep. 28, 2010 from U.S. Appl. No. 11/503,350, Behar, Systems and Methods for Monitoring Subjects in Potential Physiological Distress, filed Aug. 10, 2006.
Office Action dated Oct. 15, 2010 from U.S. Appl. No. 11/627,198, Derchak, System and Method for Identity Confirmation Using Physiologic Biometrics to Determine a Physiologic Fingerprint, filed Jan. 25, 2007.
Office Action dated Nov. 18, 2010 from U.S. Appl. No. 11/492,484, Behar, Computer Interfaces Including Physiologically Guided Avatars, filed Jul. 24, 2006.
Office Action dated Jan. 4, 2011 from U.S. Appl. No. 11/233,317, Gal, Improved Sensors for Inductive Plethysmographic Monitoring Applications and Apparel Using Same, filed Sep. 21, 2005.
Office Action dated Jan. 27, 2011 from U.S. Appl. No. 10/991,877, Keenan, Method and system for processing data from ambulatory physiological monitoring, filed Nov. 18, 2004.
Office Action dated Feb. 2, 2011 from U.S. Appl. No, 11/373,822, Sackner, System and Methods for Ambulatory Monitoring of Physiological Signs, filed Mar. 9, 2006.
Supplementary Partial European Search Report of the European Patent Office, Application No. EP 04759405.6, dated Jan. 24, 2011, 4 pages.
Office Action dated Nov. 30, 2010 from Japanese Appl. No. 2006-509897, Adidas AG, Systems and Methods for Respiratory Event Detection, with translation.
Office Action dated Mar. 29, 2011 from corresponding Japanese Appl. No. 2007-516769, with translation, 4 pages.
Office Action by European Patent Office for European Application No. 06761157.6-1657, European Patent Office, dated Oct. 22, 2014.
Fahrenberg, "Origins and Developments of Ambulatory Monitoring and Assessment", in Fahrenberg et al., 2001, Progress in Ambulatory Assessment Seattle, WA: Hogrefe and Huber.

\* cited by examiner

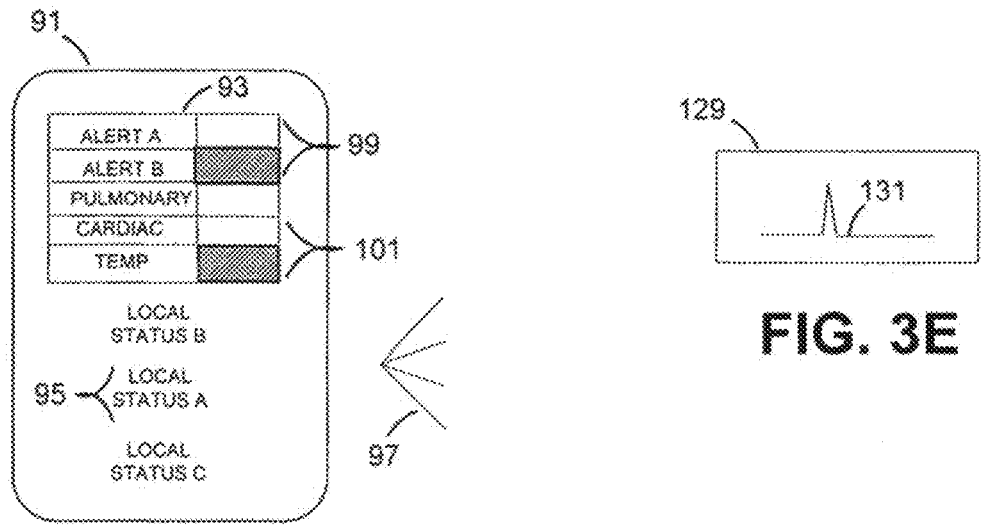
FIG. 3A
FIG. 3E
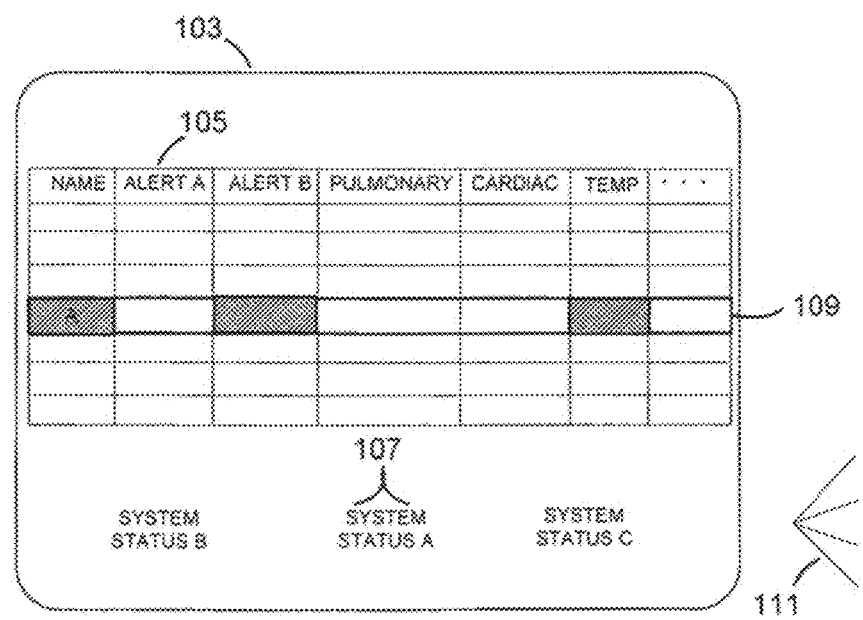
FIG. 3B

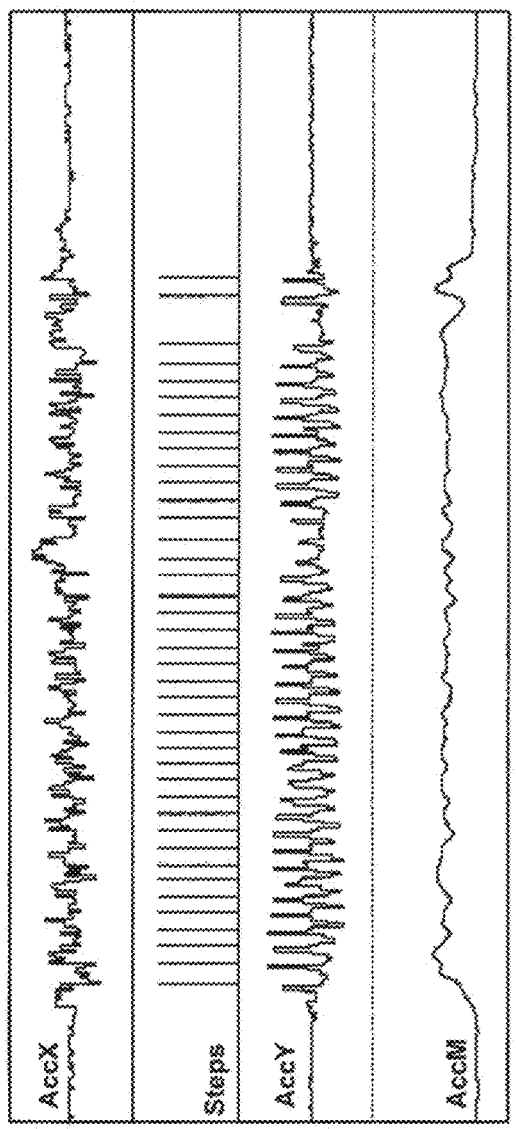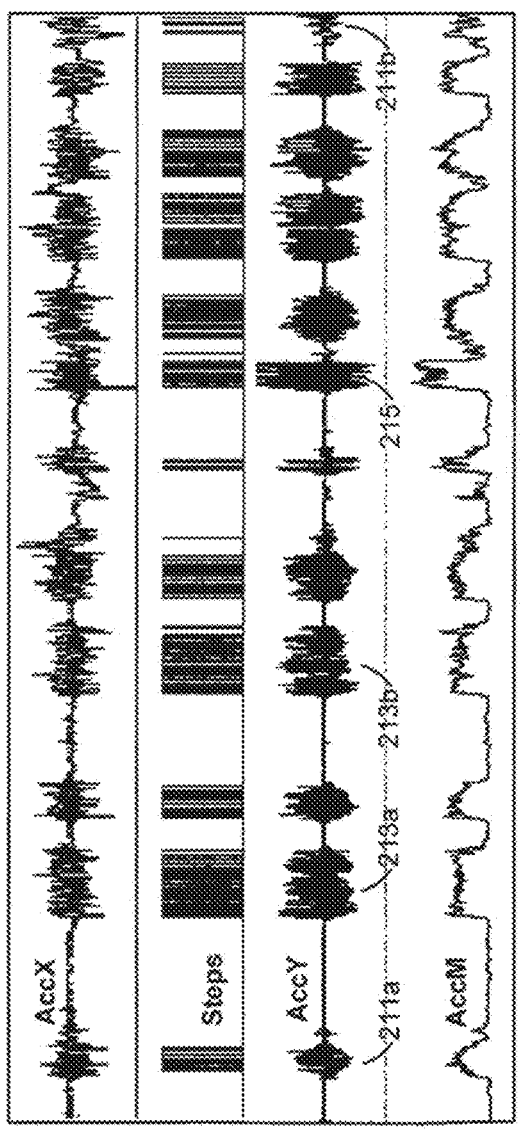

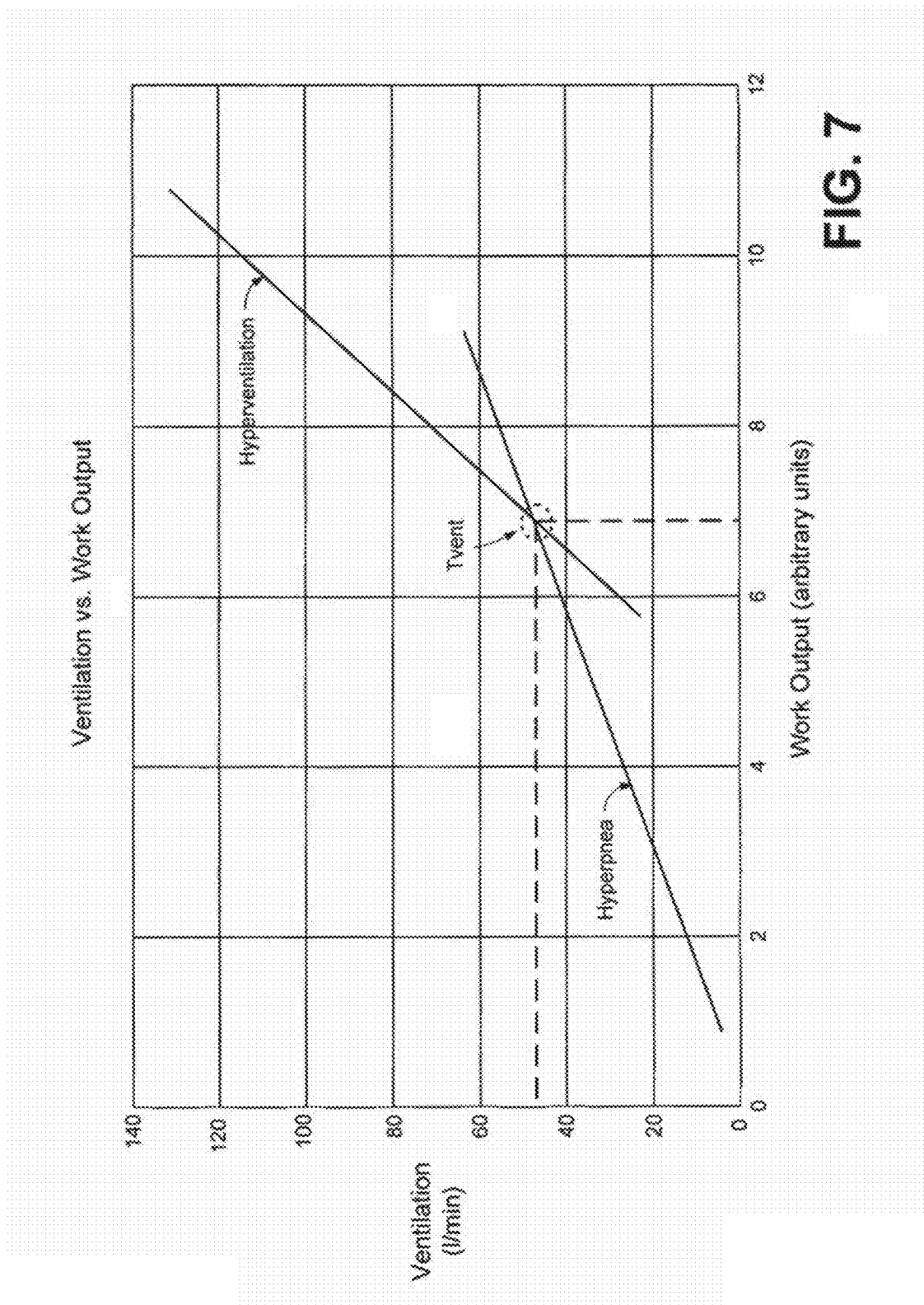

SYSTEMS AND METHODS FOR MONITORING SUBJECTS IN POTENTIAL PHYSIOLOGICAL DISTRESS

CROSS REFERENCE TO RELATED APPLICATIONS

This application is a divisional of U.S. application Ser. No. 11/503,350 filed Aug. 10, 2006, which is a continuation of prior International application PCT/US2005/021433, with an international filing date of Jun. 17, 2005 and designating the United States, which in turn claims the benefit of prior U.S. provisional application 60/580,971 filed Jun. 18, 2004 and of prior U.S. provisional application 60/580,966 filed Jun. 18, 2004. All four of these applications as well as others included herein are hereby incorporated by reference in their entireties for all purposes.

FIELD OF THE INVENTION

The present invention provides improved systems and methods for real-time monitoring and display of physiological data obtained from monitored subjects; in preferred embodiments, the invention dynamically accommodates to changing locations of both monitored subjects and monitoring personnel; physiological data includes information of respiration, cardiac activity, posture, physical activity, temperature, or the like.

BACKGROUND OF THE INVENTION

Real-time monitoring and display of physiological data from monitored subjects is now of interest in many fields of endeavor. For example, such monitoring can be useful where the monitored subjects are in potentially stressful or hazardous situations. Such situation occur in the military, in first responder professions such as firefighters, rescuers, police and the like, industrial settings, and so forth. This invention has other applications in competitive athletics during training, and competition; and in non-competitive but potentially hazardous recreations such as diving, caving, and the like; and so forth.

Systems and methods for real-time physiological monitoring are known in the prior art. For example, U.S. Pat. No. 6,198,394 B1 (the '394 patent), filed Dec. 5, 1996, discloses a system for remote monitoring directed to military applications. It describes systems that require subjects to wear a military-type harnesses that carry a variety of sensors and communication equipment. However, such military-grade equipment designed for battlefield use has limited appeal in other applications.

Other prior-art monitoring systems and methods can be more appealing for non-military use. For example, U.S. Pat. No. 6,047,203 (the '203 patent), filed Apr. 4, 2000, discloses a monitoring system in which innovative physiological sensors are arranged in comfortable and unobtrusive garments of various types and can provide quantitative data on cardiac, respiratory, and other physiologic systems. However, such systems have not been adapted to real-time operation in field conditions.

Thus, that prior art lacks monitoring systems that provide quantitative physiological data in real-time using subject-monitoring technologies appealing to a broad range of monitored subjects.

SUMMARY OF THE INVENTION

Objects of the present invention include overcoming this lack in the prior art by providing monitoring systems and methods that gather quantitative physiological data in real-time by means of subject-monitoring technologies that are appealing to a broad range of monitored subjects.

Systems of this invention preferably include one or more monitoring apparatus carrying sensors for monitoring individual subjects, and local electronic module or modules (known as local data units (LDU)) for acquiring data from the monitoring apparatus (collectively, "monitoring apparatus"). Preferably, sensors are arranged in or carried by a wearable item that can be comfortably worn by a monitored subject. Wearable items can be garments of various types, belts, caps, patches, and the like. Sensor can be arranged in or carried by a wearable item, for example, by being arranged in (open or closed) pockets, by being attached to a garment, as by sewing, gluing, Velcro, and the like, or by being integral to the garment. In the latter case, the garment can serve as all or part of one or more sensors, or can include active components such as conductive threads, stretchable loops, contacts, and so forth. The LDU operates sensors if needed, gathers sensor signals by conductive wires, threads, or other elements, or by wireless links local to the monitored subjects. It preferably also preprocesses sensor data, stores sensor data, transmits sensor data for remote use, determines selected physiological parameters, checks parameters for conditions indicating warnings or alarms, displays selected data to monitored subjects, and the like.

Many different types of sensors can be present in different embodiment of this invention that can be in turn directed to different applications. Generally, system sensors include one or more of the following types: sensors for respiratory functions; sensors for cardiac functions; sensors for blood oxygen saturations; sensors for subject posture, subject activity, and the like; sensors for skin temperatures, sensors for electroencephalographic signals; and so forth. In certain applications, sensors can also include ballistic impact microphones for registering impacts received by a monitored subject that may indicate bodily injury. Sensors can be based on the various technologies known in these arts. Preferred sensors for respiratory function are based on inductive plethysmographic technology that measures respiratory motions of the subject thorax and/or abdomen. Preferred sensors for cardiac function are based on electrical detection of heart activity, and/or also on plethysmographic technology that measures cardiac or vascular pulsations. Preferred sensors for posture and activity are based on processing data from one or more accelerometers mechanically coupled to the subject LDUs gather, preferably process, and communicate sensor data. If appropriate sensor data is gathered, LDUs preferably extract respiration rate, and/or heart rate, and/or body temperature, and/or posture, and/or indicia of activity, and/or oxygen saturation. LDUs can extract other or additional physiological parameters that may be appropriate for particular applications of this invention. For example, tidal volume and minute ventilation can be extracted from plethysmographic respiratory data. Preferably, LDUs also determine and check selected conditions indicating physiological distress or danger. More simple alarm conditions can be checked by comparing individual, extracted physiological parameters against normal ranges and bounds. More complex alarm conditions can be checked by comparing and/or correlating combinations of two or more physiological parameters against joint bounds or joint ranges. LDUs also preferably display, audibly indicate, or otherwise make monitored subjects aware of their current physiological status.

LDUs also preferably communicate some or all of the gathered physiological data to external monitoring facilities. External monitoring facilities can be near, for example less than hundreds of meters from, monitored subjects; or can be in the vicinity of, for example from hundreds to thousands of meters from, monitored subjects; or can be remote, for example more than thousands of meters from, monitored subjects. For example, LDUs may wirelessly communicate with local monitoring facilities that process and display data from communicating LDUs. Also, the local monitoring facilities may communicate by wireless or wired links to remote monitoring facilities than can further process and display data from communicating local monitoring facilities. Also, LDUs can directly communicate with remote monitoring facilities by, for example, being in wireless communication with access points having wired links to the remote monitoring facilities. This invention's systems can include additional types of external monitoring facilities and/or communication nodes. LDUs, external monitoring facilities, and other system elements also preferably cooperate to store sensor data and its interpretation for later analysis and/or audit.

In preferred embodiments, these communication links and communication patterns are dynamically established in response to current locations of LDUs, local monitoring facilities, and remote monitoring facilities (collectively, "system elements"). Since in the field locations of these system elements can change over time and often in unpredictable ways, it is also preferred that system communications adapt dynamically to such location changes. It is also preferred that system elements communicate in both directions, so that messages and processed data can be conveyed to LDUs and sensor data is being conveyed to external monitoring facilities.

In many embodiments communication bandwidth, especially wireless bandwidth, is limited, and it is therefore preferably that in normal circumstances LDUs not transmit all sensor data to local or remote monitoring facilities (and similarly for transmission between separate external monitoring facilities). In one preferred embodiment, LDUs periodically transmit only brief "OK" messages as long as no danger, warning, or other exceptional conditions id detected. Alternatively, LDUs can also transmit some or all of the physiological parameters extracted from the sensor data. In this embodiment, if a danger, warning, or exceptional condition is detected, then LDUs begin to transmit increasingly detailed data concerning the cause of the condition (if it can be determined). For example, the nature and severity of a detected condition can be then transmitted. For more severe conditions, LDUs can transmit some or all of the original sensor data.

Generally, methods of this invention monitor subjects engaged in ambulatory activities by processing physiological sensor data obtained from each ambulatory monitored subject at a location local to that subject and separately from other monitored subjects in order to determine physiological information comprising indication of whether a physiological state of said subject is normal or not and/or is acceptable or not; then by presenting one or more of said monitored subjects items selected from said physiological information; then by transmitting items selected from said physiological information from said locations local to said monitored subjects to a location remote from said monitored subjects; and finally by displaying at said remote location some or all of said transmitted physiological concerning said monitored subjects.

Monitored subjects can be in potential and/or actual physiological stress such as subject to heat stress, anxiety, panic, dehydration, and disorientation. Subjects' ambulatory activities include daily-living activities, and/or employment activities, and/or professional activities, military activities, police activities, firefighting activities, rescue activities, industrial activities, athletic competition activities, athletic training activities, and recreation activities.

Physiological parameters of interest comprise one or more parameters selected from the group consisting of parameters describing a subject's respiratory function, parameters describing a subject's cardiac function, parameters describing a subject's posture, parameters describing a subject's activity, parameters describing a subject's energy consumption, and parameters describing a subject's temperature. Physiological state can be determined by comparing individual parameters to pre-determined ranges of values, or by combining multiple parameters, e.g., by statistical regression functions, and comparing the combined values to pre-determined regions of parameter space. A subject's ventilatory threshold is preferred for establishing acceptable ranges of exertion.

In order not to overload remote external monitoring facilities (also referred to as "remote locations"), transmitted items are preferably selected in dependence on whether or not said physiological state is acceptable or not and/or is normal or not. For acceptable or normal subjects, little more than indication of normalcy can be transmitted. For other subjects, transmitted items can include some or all of said sensor data and/or said physiological information. And in order to allow flexible use of this invention in unpredictable field conditions, it is preferred than communication between its elements, e.g., those local to a subject and external remote facilities, by established and configured dynamically. Accordingly, different system elements can select the other system units with which to communicate, for example, depending on signal clarity or strength or upon unit priority, or the like. Preferably, one external remote facility can be designated, e.g., by priority, as a primary facility to eventually receive information on all monitored subjects.

Preferred system elements include portable monitoring apparatus for real-time monitoring of an ambulatory subject that includes a wearable item comprising one or more sensors, said sensors providing one or more signals responsive to the physiology of an ambulatory subject wearing said item; and a portable data unit local to said wearable item comprising a processing device that performs retrieval and processing said sensor signals in order to determine physiological information comprising indication of whether a physiological state of said subject is normal or not and/or is acceptable or not; presentation to a wearer items selected from said physiological information; and transmission items selected from said physiological information from said portable data unit to a location remote from said portable data unit, said items selected in dependence on said physiological state of said monitored subject Preferred system elements also include external monitoring facilities for real-time monitoring of ambulatory subjects including displays; communication interfaces for wireless communication; and a processing device operatively coupled to said display and to said communication interface that establishes communications with one or more portable monitoring apparatus, each portable monitoring apparatus monitoring an ambulatory subject and wirelessly transmitting physiological information concerning said subject, and receives transmitted physiological information concerning one or more monitored subjects; and displays selected items of received physiological information. External facilities generally communicate both with portable monitoring apparatus and with other external facilities. 71. A system for real-time monitoring of ambulatory subjects comprising:

A system of this invention includes these elements cooperatively communicating for real-time monitoring of ambulatory subjects, namely one or more portable monitoring apparatus; and one or more external monitoring facilities so that said portable monitoring apparatus wirelessly communicate with at least one of said external monitoring facilities, and wherein at least one external monitoring facility wirelessly communicates with at least one other external monitoring facility, and wherein said wireless communication comprises physiological information describing ambulatory subjects monitored by said portable monitoring apparatus.

The invention also includes program products with computer readable media containing computer instructions for performing the invention's methods.

A number of references are cited herein, including patents and published patent application, the entire disclosures of which are incorporated herein, in their entirety, by reference for all purposes. Further, none of these references, regardless of how characterized above, is admitted as prior to the invention of the subject matter claimed herein.

Specific embodiments of this invention will be appreciated from the following detailed descriptions and attached figures, and various of the described embodiments are recited in appended claims.

BRIEF DESCRIPTION OF THE DRAWINGS

The present invention may be understood more fully by reference to the following detailed description of preferred embodiments of the present invention, illustrative examples of specific embodiments of the invention, and the appended figures in which:

FIGS. 3A-F illustrate alternative displays of monitored sensor data;
FIGS. 4A-B illustrate processing at the monitored subject;
FIGS. 6A-B illustrate exemplary accelerometer data for a subject;
and
FIG. 7 illustrates ventilatory thresholds (referred to herein as "Tvent").

DETAILED DESCRIPTION OF THE PREFERRED EMBODIMENTS

Figure 1A:
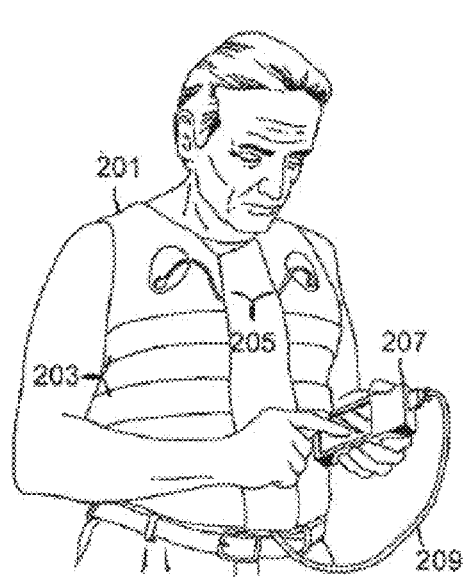
FIGS. 1A-C illustrates wearable items with sensors.

Preferred embodiments of the systems and methods of this invention are described in the following. In the following, and in the application as a whole, headings are used for clarity and convenience only.

5.2. System Components

System components of the present invention include: monitoring apparatus with physiological sensors, wearable items carrying these sensors, local data units ("LDU"), and so forth; local or remote monitoring facilities with compute, data display (for monitoring personnel), and data storage capabilities; and communications between these components. Preferred embodiments of these components are described in this subsection.

Wearable Sensors and Garments

Monitoring apparatus preferably comprises a wearable item or items, such as a garment, shirt, vest, chest strap, patch, cap, or the like, in or on which physiological sensors are disposed. Appropriate sensor technologies and their dispositions on monitored subjects are preferably chosen jointly so that resulting apparatus (for example, monitoring garments) are unobtrusive, comfortable, and even appealing to monitored subjects while providing reliable, real-time physiological monitoring data. Weight is an important aspect of comfort, and it is preferred that the monitoring apparatus and any associated electronics (e.g., LDUs) be less than about 800 g, more preferably less than 700 g, and even more preferably less than 600 g or 500 g or lighter.

One preferred respiratory and/or cardiac sensor technology is inductive plethysmography (IP), which has been clinically confirmed to provide reliable, quantitative data on at least respiratory and cardiac functions. IP sensors can be disposed on monitored subjects in various kinds of garments, for example, in bands, or in partial-shirts, or in shirts, or on partial body suits, or in full body suits, or in caps, and the like. IP-based sensors function by measuring time-varying inductance of conductive loops (often configured in elastic, expandable bands) that are placed at various levels about the thorax, abdomen, and other body parts of a monitored subject. This time-varying loop inductance reflects primarily indicia of time-varying cross-sectional areas enclosed by these loops, and using signal processing and pattern recognition techniques with reference to established physiological models (such as a two-compartment model of respiratory volumes), these indicia of cross-section areas can be processed to yield indicia or measures of physiological functions and/or times of occurrences of physiological events. For example, it is possible to obtain indicia of cardiac stroke volumes, indicia of respiratory tidal volume and minute ventilation, occurrence times of respiratory events, such as apneas, and the like, and so forth.

However, IP-based sensors are preferred and not limiting, and this invention can readily employ sensor based on alternative technologies. Certain alternative sensor technologies make, similar to IP-based sensors, make measurements reflecting cross-sectional areas, or circumferences, or their geometric equivalents, or measurement that can be converted into such information (for example, stress or strain of an expandable loop about the subject), at one or more levels through the thorax, abdomen, or other body structures, and at sample rates up to 200 Hz. Data from IP and alternative sensors can then be processed by the methods that have been developed for IP signals. For example, alternative sensors can be based on thread and fabric technologies being and to be developed: a sensor may measure the resistance of conductive threads having strain-dependent resistance that are incorporated into garments or bands; or a sensor may optically or electrically means the local stress of a fabric woven so that local stress reflects length and/or circumferential. For another example, alternative sensors may use energy radiation (such as ultrasound radiation, or electric fields, magnetic fields, or electromagnetic radiation) to measure geometric parameters (such as distances) through body structures.

However, for brevity and concreteness only, the subsequent description will be largely in terms of preferred IP sensor technologies and of processing methods sensitive to body cross sectional area (or circumference, or the equivalent). Details of the preferred IP technology, its disposition in garments, its processing and interpretation, and certain closely allied sensor technologies is described from the following U.S. patents (collectively, the "IP patents"), all of which are incorporated by reference in the entireties herein for all purposes and are assigned to the assignee of this application. Patents disclosing IP technology and its disposition in fabrics and garments (collectively, the "sensor and garment patents") include U.S. Pat. No. 6,551,252, filed Apr. 17, 2001 (an improved ambulatory IP system and sensor garment); U.S. Pat. No. 6,341,504, issued Jan. 29, 2002 (stretchable conductive fabric for IP sensors); U.S. Pat. No. 6,047,203, issued Apr. 4, 2000 (an ambulatory IP system including a sensor garment); U.S. Pat. No. 5,331,968, issued Jul. 26, 1994 (IP sensors and circuitry); U.S. Pat. No. 5,301,678, issued Apr. 12, 1994 (stretchable IP transducer); and U.S. Pat. No. 4,807,640, issued Feb. 28, 1989 (stretchable IP transducer).

Patents disclosing processing of IP signals to obtain measures of respiratory function (collectively, the "data processing and interpretation patents") include U.S. application Ser. No. 10/457,097, filed Jun. 6, 2004 (object oriented methods for monitoring of physiological parameters); U.S. Pat. No. 6,413,225, issued Jul. 2, 2002 (improved methods for calibrating IP breathing monitors); U.S. Pat. No. 6,015,388, issued Jan. 18, 2000 (methods for measuring respiratory drive providing various outputs, including control signals for mechanical ventilators or continuous positive air pressure (CPAP) devices); U.S. Pat. No. 5,159,935, issued Nov. 3, 1992 (measurements of individual lung functions); U.S. Pat. No. 4,860,766, issued Aug. 29, 1989 (noninvasive methods for measuring and monitoring intrapleural pressure in newborns by surface IP of cranial bones); U.S. Pat. No. 4,834,109, issued May 30, 1989 (methods for calibrating IP breathing monitors); U.S. Pat. No. 4,815,473, issued Mar. 28, 1989 (methods for monitoring respiration volumes); U.S. Pat. No. 4,777,962, issued Oct. 18, 1988 (methods and systems for distinguishing central, obstructive, and mixed apneas from signals which monitor the respiratory excursions of the rib cage and the abdominal); U.S. Pat. No. 4,648,407, issued Mar. 10, 1987 (methods for detecting and differentiating central and obstructive apneas in newborns); U.S. Pat. No. 4,373,534, issued Feb. 15, 1983 (methods for calibrating IP breathing monitors); and U.S. Pat. No. 4,308,872, issued Jan. 5, 1982 (methods for monitoring respiration volumes).

Patents disclosing processing of IP signals to obtain measures of cardiac function include (collectively, the "cardiac function patents") U.S. application Ser. No. 10/107,078, filed Mar. 26, 2002 (signal processing techniques for extraction of ventricular volume signal); U.S. Pat. No. 5,588,425, issued Dec. 31, 1996 (methods and systems for discriminating between valid and artifactual pulse waveforms in pulse oximetry); U.S. Pat. No. 5,178,151, issued Jan. 12, 1993 (methods for IP measurement of cardiac output); U.S. Pat. No. 5,040,540, issued Aug. 20, 1991 (IP measurement of central venous pressure); U.S. Pat. No. 4,986,277, issued Jan. 22, 1991 (IP measurement of central venous pressure); U.S. Pat. No. 4,456,015, issued Jun. 26, 1984 (IP measurement of neck volume changes); and U.S. Pat. No. 4,452,252, issued Jun. 5, 1984 (determining cardiac parameters from neck and mouth volume measurements).

Preferably, such IP-based and similar or equivalent physiological sensors are disposed it unobtrusive, comfortable, and non-restricting fabric structures and wearable items, such as garments and/or bands, that are worn by a monitored subject. This invention includes a variety of wearable items and sensor dispositions therein, the particulars of which depend primarily on the type and extent of physiological monitoring. Wearable items include garments, shirts, vests, bands, caps, patches, and the like, all with one or more sensors. Associated with a wearable item is a local processing/storage/communication device unit (LDU) that serves to retrieve sensor data using wired or wireless link to the sensors carried by the wearable item, to preprocess the sensor data, and to relay selected data to external monitoring facilities and personnel. An LDA also can serve to perform assessment of the subject's physiological condition, to output data to the subject, and to receive subject input. Typically, the LDU is carried by a subject separately from a garment or band, but can also be carried in or on or incorporated into the sensor garment (e.g., in the form of wearable electronics as known in the art).

Figure 1B:
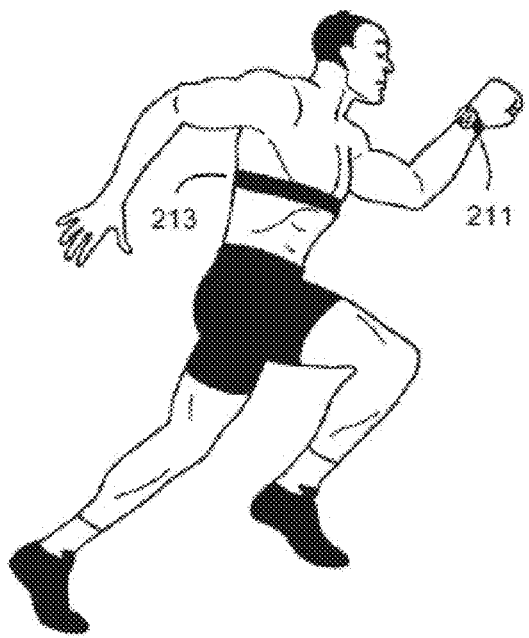
Figure 1C:
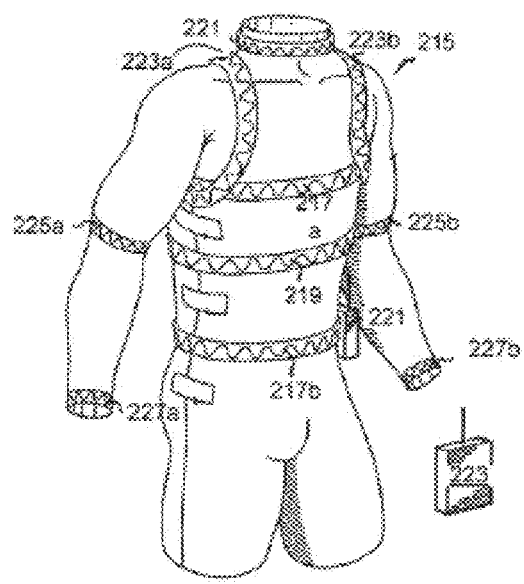

FIGS. 1A-C illustrate several wearable items preferred for differing monitoring applications. FIG. 1A illustrates typical configuration 201 in which a half-shirt, or vest, or similar, includes at least two sensor bands 203 (e.g., IP based), as well as other sensor types, such as ECG electrodes 205, thermistors, accelerometers, and the like (not illustrated). Sensor bands 203, if positioned at the rib cage and abdomen, provide at least respiratory rate and respiratory volume information. If positioned at the mid-thorax, both respiratory and cardiac data can be provided. Separate LDU 207 provides for output to and input from the subject, and is connected to sensors by wired link 209. The item can be less than approximately 750 g or lighter.

FIG. 1B illustrates a more simple wearable item configured as single 213 band that can carry multiple sensors, for example, a single IP-based sensor band (or equivalent), ECG electrodes, as well as other sensor types such as described above. LDU 211 is configured in a convenient wristwatch-like form and is wirelessly linked to the sensors, for example, by a Bluetooth-like network or similar. This LDU has more limited capability for subject input and output. This illustrated configuration can have substantially less weight than that of FIG. 1A, being, for example, less than approximately 400 g or less.

Alternatively, LDU 211 can be configured to be carried in or on or integral to band 213. A subject can then quickly and easily begin physiological monitoring by simply placing such a combined band about the torso. Further, such a combined band-LDU can be advantageously jointly configured to be attached to or to accompany various types of garments so that ordinary garments not initially contemplated for use in physiological monitoring can be easily equipped with monitoring capabilities. Attachment can be by Velcro, snaps, zippers, and the like. Sufficiently elastic bands can also accompany garments without special attachments. For example, subjects wearing the usual wet suits, bicycling shirts, football uniforms, and other athletic clothing can be easily monitored; similarly subjects in first responder services, public protective services, military services, and the like can be physiologically monitored without modification to their standard apparel. For more extensive physiological monitoring, ordinary garments can be accompanied by or attached to two or more sensor-LDU combinations. For example, a second band about a subject's torso can provide more accurate respiratory monitoring as well as carry additional physiological sensors of other types. This invention also includes kits of two or more such sensor-LDU combinations. Different combinations can multiply monitor single physiological systems (e.g., respiratory systems) or can monitor different physiological systems (e.g., respiratory systems and cardiac systems). Each combination is configured to accompany or be attached to ordinary apparel. Kits of this nature are advantageous where specific physiological monitoring for ambulatory is usefully assembled as needed and even "on the spot".

FIG. 1C illustrates a suit-like (or partial suit-like) garment covering a large fraction of the subject's torso and capable of carrying a wider range of physiological sensors. For example, the garment could be designed as a wet suit used for use in diving, or as a fabric structure for other uses. Bands 217a and 217b (e.g. IP based) about the rib cage and abdomen bands provide respiratory data; bands 223a and 223b provide further data on the relative functioning of the left and right lung. Band 219 at mid-thorax provides cardiac output data. Neck band 221 provides data on carotid arterial and jugular venous pulsations from which further cardiac data can be determined. Bands 225a and 225b and bands 227a and 227b provide brachial and radial pulsation data, that can be used, for example, for assessment of peripheral blood flow. Other bands and sensors not illustrated can also be incorporated in this garment. Unit 221, which advantageously is carried in a pocket or similar of the garment, collects sensor data for wireless transmission to another nearby LDU unit 223 or external monitoring facility unit 223. If configured as an LDU, unit 223 may be carried by the monitored subject and forward data to the remote external monitoring facility. Alternatively, unit 223 can be local external monitoring facility that is located some tens to hundreds of meters from the monitored subject and that provides status to local monitoring and emergency-response personnel. Such an external monitoring facility can optionally receive data from more than one monitored subject.

The wearable items illustrated in FIG. 1 are exemplary indications of how various monitoring needs can be accommodated and are not limiting. For example, an alternative wearable item is a shirt similar to that of FIG. 1A but with only two respiratory IP bands, where details of cardiac function are not needed. Other example are garments adapted and designed for women. For example, an adaptation of the strap of FIG. 1B can be a sports bra with sensors with one or more sensor bands; a garment similar to the shirt of FIG. 1A may be designed as a corset.

Further, wearable items can incorporate other sensors types when needed. These can include, for example, sensors for chemical exposures (CO, $CH_4$, and the like), sensors for biological hazards (various kinds of radiation, of organisms, and the like), sensors for electroencephalograms, electrooculograms, and the like, and other sensors. Details of IP-based wearable sensors and garments are disclosed in the sensor and garment patents and/or the cardiac function patents.

System Structure

Data from subjects monitored with the sensor and garment technologies of this invention is preferably presented both locally to the monitored subjects and also remotely at one or more external monitoring facilities to monitoring personal who monitor the physiological statues of the monitored subjects. In most embodiments, the monitored subjects and the monitoring personnel are spatially or geographically dispersed over various distances, requiring that monitoring systems of this invention provide for remote communications as well as for data processing and display.

Figure 2A:
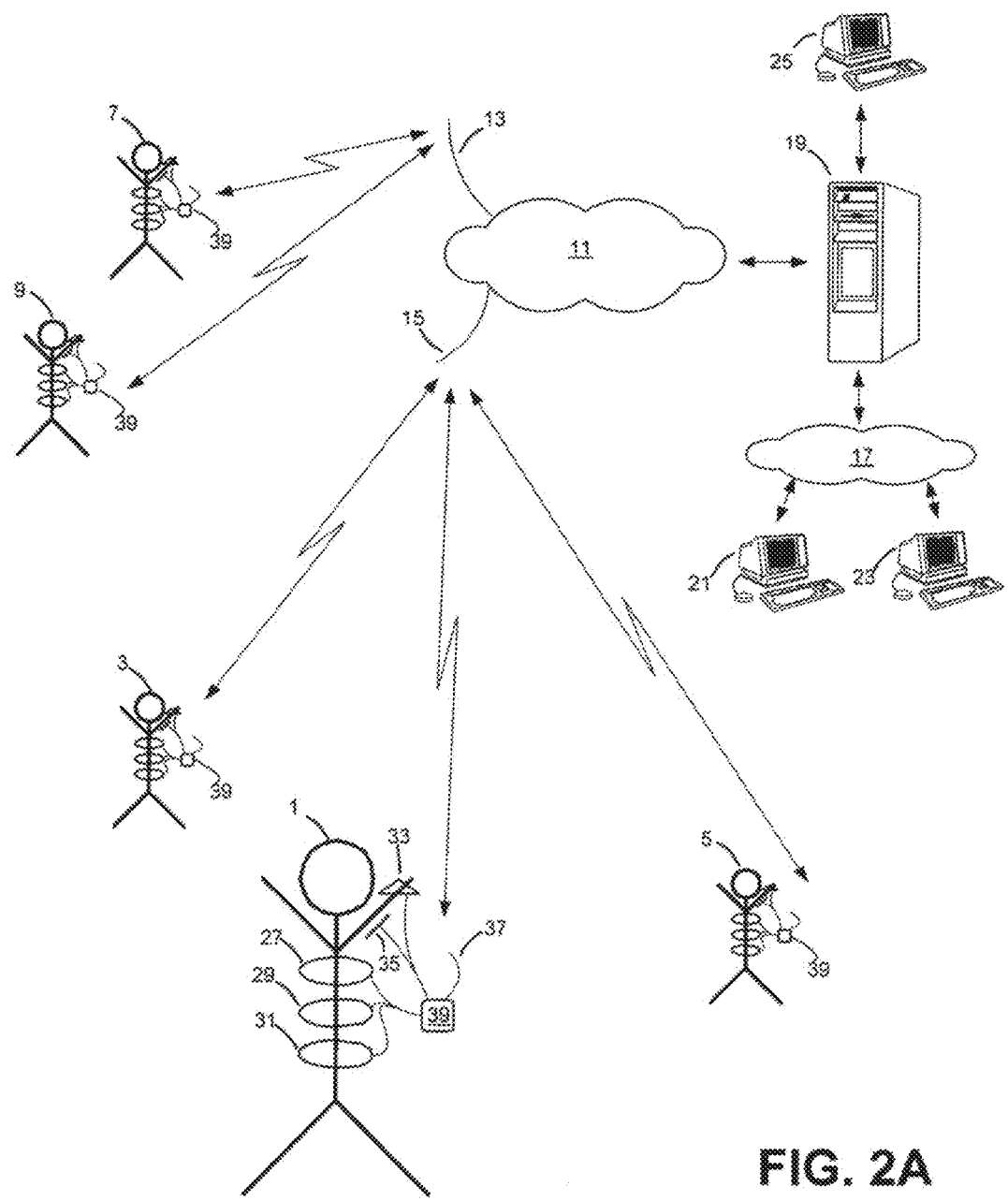
FIGS. 2A-B illustrate embodiments of real-time monitoring systems.

FIG. 2A illustrates one preferred embodiment of a more centralized monitoring system structure. Here, monitored subjects 1, 3, 5, 7, and 9 are monitored by remote monitoring personnel at displays 21, 23, and 25 linked to a single external monitoring facility 19. Embodiments of such a system may concurrently monitor from 1 to 10 or to 100 or more subjects. The monitoring apparatus (sensors, garment, and LDUs) are schematically illustrated here as being generally similar; in other embodiments different monitoring apparatus may be used and different subjects may be equipped with different types of monitoring apparatus. For example, certain subjects may be equipped with IP-based sensors, while other subjects may have similar, equivalent sensors of other types. Also, certain subjects may be fitted for more complete monitoring (for example, with the garment of FIG. 1C), while others may be fitted with for an intermediate level of monitoring (for example, with the garment of FIG. 1A), while still others may be fitted for only basic monitoring (for example, with the garment of FIG. 1B). For such heterogeneous systems to function smoothly, it is preferably that the various LDUs 39 data identifying the type of monitoring apparatus, perhaps in self-defining formats that can be interpreted by external monitoring facility 19.

Monitored subject 1 is fitted with a garment similar to that of FIG. 1A, which is illustrated in more detail that garments of the other subjects. In particular, bands 27 and 31 are rib cage and abdominal bands for providing respiratory rate, and/or respiratory volume, and/or recognition of respiratory events (e.g., coughing, gagging, and the like). Optional band 29 provides cardiac output data. Sensor 33 generally represents sensor types touching the subject, such as a pulse oximeter attached to a finger, ear lobe, or other body part or an accelerometer mechanically coupled to the subject. Sensor 35 generally represents sensors types in contact with the subject, such as ECG leads, heart rate sensors, thermistors, and the like. Not illustrated are other sensor types, such as a geographic position sensor that can be a GPS device. (Although optional, portions of the following description assume the existence of geographic position data.)

Preferably, monitoring data is wirelessly transmitted from LDUs at the monitored subjects to remote monitoring personnel at external monitoring facilities. In FIG. 2A, antennas 37 on LDUs 39 are in wireless contact with one or more receivers or access points 13 and 15, from which data is forwarded to external monitoring facilities systems 19 over wired and/or wireless network 11. Network 11 can be a private or shared wired network, can be implemented though cellular phone systems, can use satellites, can use longer range wireless technologies, or the like. The access points can mutually interconnected in order to cooperatively relay data to network 11 and on to the external monitoring facilities. External monitoring facilities 19 store, process and format received data for display at monitoring stations 21, 23, and 25 linked to the facility. Here, station 25 is at the external monitoring facility site, while stations 21 and 23 are more remotely located and accessed over further networks 17. Processing at external monitoring facility 19 can be limited to duplicating, checking, or extending that already done at the LDUs, or can include use of automatic medical monitoring and diagnostic methods known in the art. All communications, especially wireless communications, are preferably encrypted to insure security and privacy.

Figure 2B:
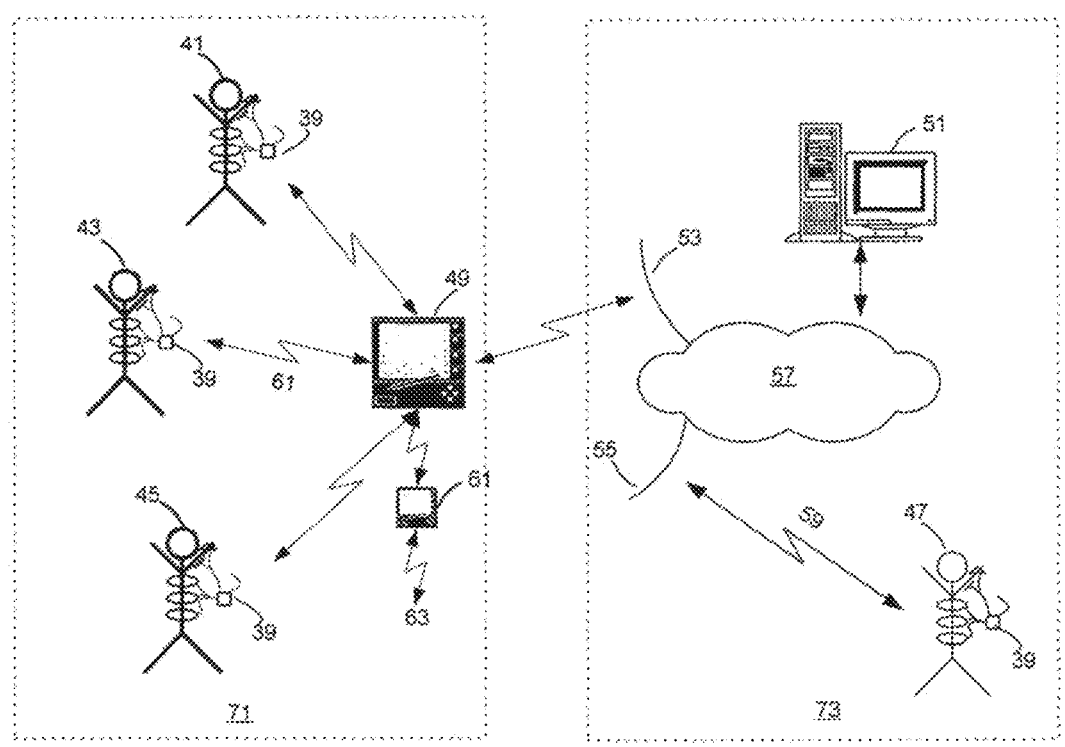

FIG. 2B illustrates another preferred embodiment of a more decentralized system structure in which data storage and processing functions are distributed between monitoring subsystems such as subsystem 71 more local to monitored subjects and monitoring subsystems such as subsystem 73 more centralized and possibly more remote from monitored subjects. Here, monitoring subsystem 73 includes structures similar to the system of FIG. 2A, for example, a remote external monitoring facility 51 with server-type computer(s) that directly communicates with and directly monitors subjects 47 located remotely from the facility, for example by being thousands or meters or more from the facility. Subject data flows directly to this external monitoring facility and its server computer(s) over wireless 59 and/or wired 57 communication networks. Optionally messages can be returned to the monitored subject from monitoring personnel at facility 51. In an alternately communication means, monitoring data can be communicated by recoding on removable computer readable media at each monitored subject 47, which are then physically transported to external monitoring facility 73. Wired communications can also be used if feasible for a particular embodiment.

Monitoring subsystem 71, instead, is directed to monitoring subjects, such as subjects 41, 43, and 45, who are in each other's vicinity and also in the vicinity of the external monitoring facility 49, for example, by all being within hundreds to thousands of meters of the facility. Here initial monitoring can be performed at local first-level monitoring facility 49, which is sufficiently near to, or in the vicinity of, the monitored subjects to be in direct contact with the monitored subjects' LDUs. Further, other external monitoring facilities in subsystem 71, such as facilities 61 and 63, can be in communication with facility 49. In such a configuration, facility 49 can act as a principal monitoring facility for all subjects in communication with facilities 49, 61, and 63.

External local monitoring subsystems can be advantageously deployed, for example, with teams of monitored subjects that work together in conditions where quick response is needed subjects with adverse physiological conditions, or with teams of monitored subjects that must move about to accomplish their tasks, or in staging areas where monitored subjects come and go unpredictably, and the like. Further, external local monitoring subsystems can also be advantageous in harsh or remote environments where communication with a central monitoring system is unreliable, subject to disruption, or from time-to-time impossible. Such subsystems can advantageously accompany teams of first responders who must move in possibly dangerous environments; or with autonomous military units. External local monitoring subsystems or a single local monitoring subsystem, can also be advantageous where only a limited number of nearby subjects need to be monitored. For example, a single external local monitoring subsystem alone can be used in sports contests to monitor teams of players.

To meet these and other similar needs, external local monitoring facility 49 is preferably self-contained, portable, and sufficiently rugged for those environmental conditions to which it is likely to be exposed. The facility preferably has sufficient capability to display status of monitored subjects and to process data directly received from subjects with LDUs of limited capability at least to the extent that the subject can be classified as OK or as not OK. Most preferably wireless communications between subjects 41, 43, and 45 and device 49 employs a dynamic protocol allowing an external monitoring facility to dynamically establish contact with the monitored subjects in range. Further, the communication protocol preferably allows a local monitoring facility to establish communications with other monitoring facilities, either other local monitoring facilities, or, when available, with a selected centralized monitoring subsystem, such as subsystem 73. In such configurations, the local facility forwards data from monitored subjects 41, 43, and 45 to central subsystem 71, either directly or via other local monitoring facilities.

Local external monitoring facilities preferably are built from hardware similar to that now used for pen-input-type and other similar PC computers, including, for example, commercially available processors, hard discs, LCD displays, wireless communication components, and the like. These devices, such as device 49, can be packaged similarly to pen-input computers; or alternatively can be packaged to meet particular needs. Alternatively, local external monitoring facilities can be packaged similarly to handheld devices, personal digital assistants, and similar devices. Facility LDU 223 (FIG. 1C) is exemplary of such facilities.

Turning to local data units (LDU), such as LDUs 39, these units include processing and communications capabilities including one or more of the following. First, LDUs advantageously select the type and amount of data transmitted on to external monitoring facilities according to selected criteria. One preferred criteria is the physiological status of the subject. Further, heterogeneous LDUs are advantageously capable of functioning together in a single monitoring system without little if any prior configuration. Thus, LDUs can transmit data to external monitoring facilities in self-defining or pre-defined formats, perhaps by including data-format identifiers in the transmitted data. Also, transmitted data can include data identifying the monitored subject.

Further, LDUs advantageously have subject display capabilities, so that selected physiological data can be immediately displayed to the monitored subject, and subject input capabilities, so that subjects can enter notes and observations. Further, LDUs advantageously exchange messages in both directions with external monitoring facilities. Monitored subjects and remote monitoring personnel can then communicate without additional devices; also remote monitoring facilities can exchange status information, such as low-battery or other hardware warnings, and also LDUs can respond to commands from remote monitoring facilities, such as request controlling data to be transmitted.

One or more of the following optional features can the appeal and usefulness of subject monitoring apparatus. First, subject input and output facilities may be detached from a main LDU unit and disposed for a monitored subject's comfort, convenience, and ready access. For example, the LDU LCD display module (or a separate module can be provided) may detach from a main LDU unit (such as 207 in FIG. 1A) and be mounted in as a heads-up display by attachment to a subject's glasses or goggles, hat, helmet, headband, other equipment, or be carried in a wrist-watch-like configuration (for example, 211 in FIG. 1B) otherwise. Separate monitoring device modules, such as the LDU itself, its input/output facilities, one or more sensors, and the like, preferably include independent battery (or other power source) and wirelessly intercommunicate using very short range, very low power radio links (for example, using ZigBee technology (www.zigbee.org, last visited Jun. 10, 2004)), or ISM low frequency transmission, or the like. Further, an LDU may have audible and/or tactile alarms and/or other user interface devices, also optionally detachable from a main LDU unit.

Preferred Communication Facilities

Communications links and paths between LDUs and external monitoring facilities, between external monitoring facilities themselves, and between external monitoring facilities and/or LDUs with principal or centralized external monitoring facilities preferably are automatically self-organizing to accommodate unpredictable and changing locations of these subsystems and facilities. Such as function is particularly advantageous in monitoring system with where one or more configurations similar to that illustrated as 71.

In one embodiment, LDUs and external monitoring facilities exchange identification and control messages. Identification messages provide to their receivers the identity and type of the broadcaster. Control messages command the receiver to communicate directly with the broadcaster. For example, a particular external monitoring facility may command that a particular receiving LDU directly communicate only with the broadcaster. A receiving LDU accepts such a command from one of the broadcasting external monitoring facility (if more than one) according different possible protocols. For example, an LDU may accept control of the nearest monitoring subsystem, perhaps as determined by signal strength. Accordingly, external monitoring facilities establish "cells" in which they act as the external facility for all LDUs that happen to be present in the cell. This protocol acts similarly to cellular phone networks. Alternatively, external monitoring facilities are assigned priorities, and a receiving LDU accepts control only from the external monitoring facility having a prescribed priority, perhaps the highest priority received by the LDU. In a combined protocol, an LDU in a particular cell accepts control from monitoring subsystems in this cell having the proper priorities. Once an LDU has accepted control from a external monitoring facility, that facility exclusively receives and/or process and/or retransmits data from that LDU. Preferably, an LDU also accepts further commands from its controlling external monitoring facility that, for example, select the data the LDU transmits. A "data triage" function to be subsequently described can be based on this capability.

A simple monitoring system include only a single external monitoring facility controlling one or more LDUs. Most extensive monitoring systems include two or more intercommunicating external monitoring facilities. In one embodiment of such systems, one external monitoring facility is designated as a primary monitoring facility, and the other external monitoring facilities accept control only from the primary monitoring facility in order to retransmit received data, exchange messages, and accept commands. In such a two-level monitoring system, monitored subjects are first monitored at their controlling local external monitoring facility, while all subjects can be monitored at the principal monitoring facility.

In another embodiment, one or more external monitoring facilities are designated as "intermediate external monitoring facilities". Intermediate external monitoring facilities then seek and accept control from one or more principal external monitoring subsystems; "regular" external monitoring facilities seek and accept control from one of the intermediate monitoring facilities; and LDUs seek and accept control from one of the regular external monitoring facilities. For example, regular external monitoring facilities in range of, or in the cell controlled by, an intermediate external monitoring facility then and communicate directly with that intermediate external facility, and through that intermediate external facility with the principal external facility. Here, subjects are monitored at two external facilities. Other intercommunication topologies can be employed if advantageous in particular embodiments.

Optionally, external monitoring facilities can cooperate with each other in a peer-to-peer manner and without control of, or relay through, a designated external monitoring facility. FIG. 2B illustrates a local external facility 61 in communication both with external facility 49 and possibly with other local external monitoring facilities 63. Peer-to-peer cooperation allows data from subjects being monitored by external facilities 61 (and 63) to be passed to central external facility 73 even if the external facilities 61 (and 63) is not in direct communications with facility 73. Similarly, messages may be passed from the central facility to directly or indirectly linked monitoring facilities. Such peer-to-peer cooperation and communication can conform to one of the ad hoc networking protocols now available in the art (generally known as "smart dust" and similar).

In military applications, monitoring personnel at regular external monitoring facilities are medics in the field or at a combat casualty screening area who provide immediate attention to subjects in immediate need. Intermediate external monitoring facilities can be at "command-posts" where the status of subjects monitored by several regular external facilities is available. The designated, central external facility can be at a headquarters location. With dynamically configuring communications, such as a monitoring system adapts to changing circumstance and need not be defined in advance.

In this case, a medic carrying a portable external monitoring facility automatically controls and receive data from LDUs of soldiers in range. If a command post external monitoring facilities is present, it automatically receives data directly from the medics in range and indirectly from soldiers in range of the medics. Headquarter can then access all the medics and command posts in range. Communication and links and control change as the various external facilities move so that, for example, when a medic approaches a group of soldiers or a combat casualty screening area, the external monitoring facility carried by the medic automatically has data on the condition of everyone in the area. With the "data triage" feature to be described, the medic receives data and be able to attend to those most in need.

5.3. Processing Methods of this Invention

This subsection describes preferred processing in LDUs and external monitoring facilities. Monitoring data displays are described subsequently.

Preferred LDU Processing/Communication Methods

Generally, it is advantageous to distribute this invention's processing from more central network elements, e.g., external monitoring facilities, to more peripheral network elements, e.g., LDUs. Monitoring results determined from sensor data processing are thereby made available more locally to monitored subjects and, communication bandwidth between network elements can be preferentially allocated to data from monitored subjects determined to be in need. Subject need is usually a function of their physiological status.

FIG. 4A illustrates in more detail preferred LDU processing. Alternatively, where LDU capabilities are limited, some or all of the illustrated processing can be performed by external monitoring facilities with results being transmitted back to the LDU. A first LDU processing function is to receive and preprocess sensor data 159. Typically, various sensors are arranged to monitor the subject including one or more of the following: respiratory sensors provide respiratory data 151; cardiac sensors provide cardiac data 151; cardiac sensors provide cardiac data 151, accelerometers provide posture and activity data 155; additional sensors for subject temperature and other physiological parameters or for aspects of the subject's environment, or the like can provide additional data 157 in various embodiments. More detailed descriptions of sensor data processing can be found in the "data processing and interpretation patents" and in the "cardiac function patents" previously included by reference.

Sensor data preprocessing includes such steps as analog domain filtering of sensor signals (as needed), digitization of analog signals, and digital preprocessing in order to, for example, select relevant signal frequency ranges, limit artifacts, and the like. For example, frequency-domain filtering respiratory signals can limit frequencies not normally present in such signals so that spurious non-respiratory signal components are reduced. Time-domain filtering, perhaps triggered by accelerometer and/or cardiac signals input can reduce broadband spurious cardiac and/or motion artifact components. Digitized sensor data is preferably stored locally 167 so that it can be later transmitted, for example, in case of temporary communications interruptions, and/or later analyzed. Sufficient storage is available on current micro-hard-drives or compact flash and similar memory cards.

Next, from the preprocessed sensor data, the LDU preferably determines key physiological parameters and trends 161. For example, respiratory rate and respiratory volume can be determined from data provided by a single sensor band (e.g., IP-based band) about the thorax. Combining data from a second IP band about the abdomen, respiratory volume can be determined with increased accuracy. Heart rate, R-wave occurrence, and the like can be readily determined form one or more lead electrocardiogram (ECG) data. Indicia of posture and/or activity can be determined from one, preferably at least two, accelerometers arranged on the monitored subject. Posture is then reflected in low-pass filtered accelerometer data, while activity is reflected in high-pass filtered data. Data from impact microphones can be analyzed to determine whether or not the subject has experienced possibly injurious impacts. On the other hand, data from certain sensors, such as body or environmental temperature, may by useful with little or no additional processing. Trends, rates, and the like can be routinely determined from multiple determinations of such physiological parameters and also stored 167.

Next, the LDU evaluates general physiological status 163 of the monitored subject using the previously determined parameters and trends. processing step evaluates the general physiological status of the monitored subject. Preprocessed sensor data is analyzed to ascertain whether the subject's physiological status is "OK", that is no physiological, normality is ascertained and/or physiological status is stable, or "not OK", that is one or more potential or actual physiological abnormalities are ascertained and/or physiological status is declining (collectively referred to as "alarms"). Advantageously, the LDU also determines the reasons and severity of not-OK subjects and/or possible future risks for OK subjects.

In one embodiment, such determinations includes comparing selected parameters and trends with thresholds and ranges of these parameters and trends that have been determined to represent OK or not OK status. For example, simple alarms can depend on values of single parameters, for example, whether or not respiration rate, or cardiac rate, or temperature, or the like, are out of normal ranges. Alarm ranges may be adjusted in view of parameter trends, for example whether trends indicate a transient or a long-term out-of-range condition. For example, an alarm may also reflect that at least one of a set of several other alarms has been found.

In preferred embodiments, these determinations depend joint values of two or more parameters or trends. For example, alarms can depend on the joint values of two or more parameters, and can be evaluated as rules depending on logical combinations of single parameter value tests. An elevated cardiac parameter and accelerometer-indicated inactivity may indicate an alarm of increased severity. More preferably, current and past values of multiple parameters and trends are selected and grouped into a sets or vectors that can be considered to belong to a space of physiological parameters. Pattern classification techniques can be used to identify in advance regions of this space which define OK and not OK status, and current subject status is determined according to which region the subject's current parameter vector lies. Finer sub-division into additional regions can identify additional alarm conditions. Pattern classification methods include statistical and/or neural network methods applied to a samples of parameter data. Finally, with sufficient LDU resources, more complex medical decision making methods known in the art may be applied to the monitored sensor data.

Sensor processing and status determination can optionally be advantageously adapted or personalized for individual monitored subjects. For example, methods parameters can be optimized, alarm thresholds can be selected by initial trials with an individual subject, and can be later used by LDUs monitoring that subject. Personalization data such as parameters, thresholds, subject identification, and the like can be delivered to the LDU on computer readable medium or may be supplied in messages from monitoring subsystems.

LDU processing function preferably adapts to monitoring subject status. For example, if a subject is determined to be not OK (or abnormal) and a reason can also be determined, the LDU preferably processes data from pertinent sensors more completely while processing less pertinent sensor data less completely. Thus should respiratory function be found to be abnormal, the LDU can sample and process data from accelerometers, temperature sensors, sound sensors, and similarly apparently less pertinent sensors less frequently.

The LDU also optionally displays 165 portions or all of this data to the monitored subject. Any or all of general physiological status, physiological alarms, parameter values and trends, and general and system information can be formatted and displayed on an LCD screen 169 visible to the monitored subject and in communication with the LDU. Information presentation formats are described subsequently. Steps 159, 161, 163 and 165 are periodically repeated in order have current sensor data. The LDU can optionally also check for and act on user input and commands.

Figure 4B:
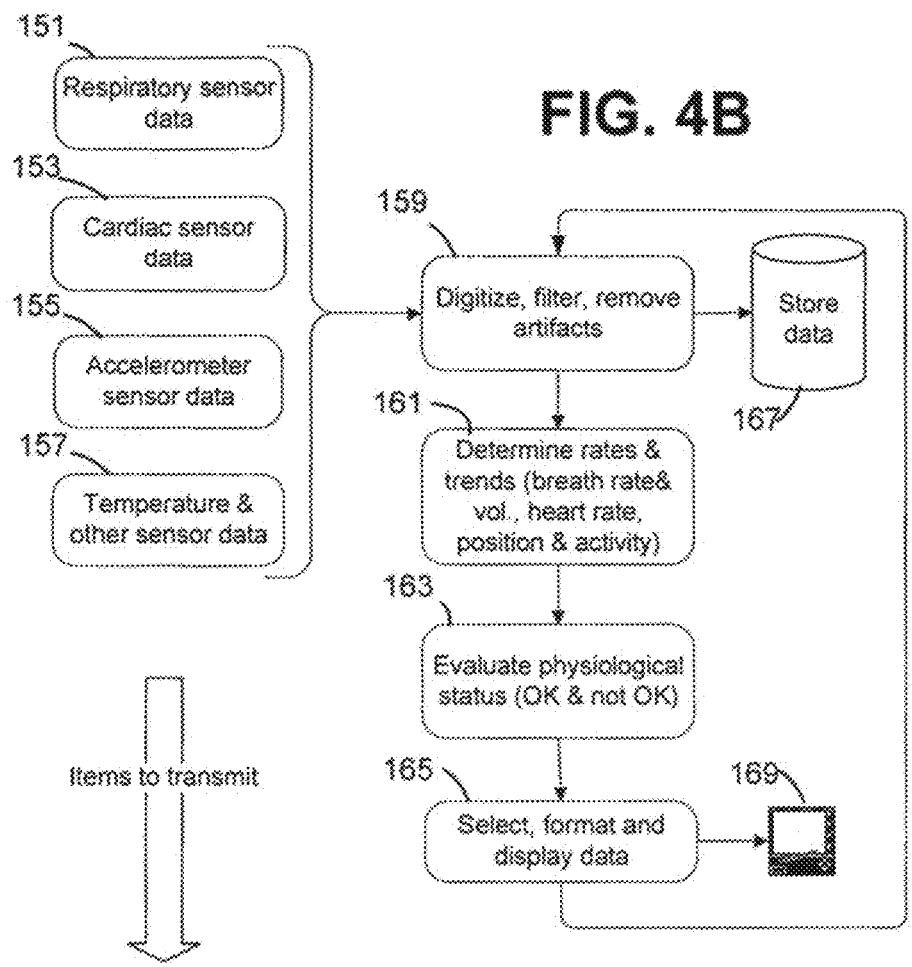
Figure 4B:
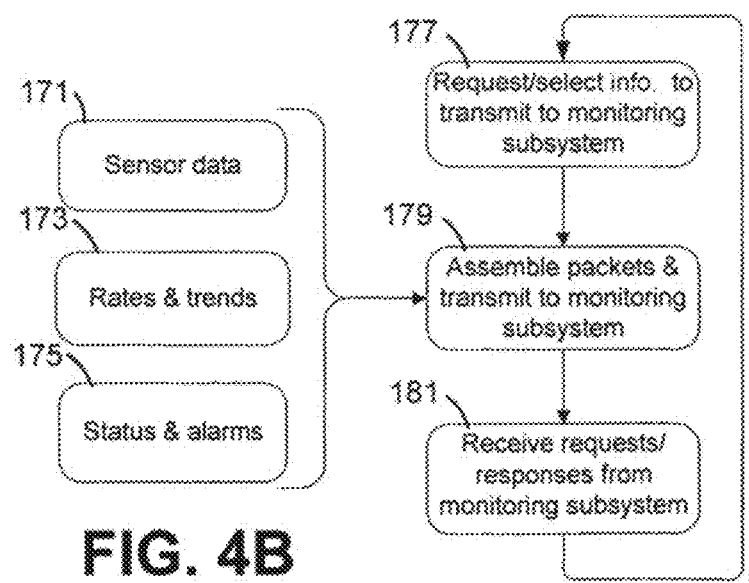

FIG. 4B illustrates in more detail preferred LDU communication functions. LDU specific communication processing and management are next described, and monitoring subsystem communication processing and management are described subsequently. Preferably, LDUs and their external monitoring facilities cooperate so that each LDU controlled by an external facility transmits needed information and the controlling monitoring subsystem received important information. In less preferred embodiments, LDUs may not have sufficient capacity to determine whether or not its monitored subject is OK and/or may transmit a fixed amount of data regardless of subject status.

Information transmitted by the LDU is selected 177 according to need, and need is preferably determined in dependence on the physiological status of the monitored subject. If the subject's status is OK, the LDU can remotely transmitted data limited to parameters, trends, and so forth. Transmitted data can be additionally limited so that an LDU periodically transmits only short "I'm OK" messages. The period can be selected to be usually between one-half and five minutes. If the monitored subject is not OK (or abnormal), additional information is preferably transmitted including at least the cause and severity of the not-OK (or abnormal) condition if determined by the particular LDU. Further, sensor data pertinent to the not-OK condition can be transmitted, or even all sensor data can be transmitted. These selections for data transmitted are exemplary of the many other selections possible that are advantageous for specific applications.

LDUs preferably transmit such additional detailed data only when permitted by the external monitoring facility. Accordingly, when the LDU detects change in monitored subject status, it uses messages to notify the external monitoring facility and to request permission to transmit additional pertinent data. The external facility then either grants or denies permission to transmit. The external monitoring facility than can direct the LDU what additional data, if any, to transmit, or the LDU may transmit it determined pertinent. Less preferably, the LDU can simply transmit selected data depending on monitoring subject status regardless of whether or not its controlling monitoring subsystem approves.

Alternately, the controlling external facility can request an LDU to transmit selected data regardless of subject status. A particular external facility may request commencement of selected more detailed data transmission, and the LDU responds by transmitting the requested data. The external facility can later request cessation of such transmission, after which the LDU returns to normal transmission of abbreviated data. Or an external facility may request certain data for a certain past time period, for example, heart rate data from 14:00 hours to 16:00 hours. In this case, the requested data is retrieved from LDU storage and sent to the external facility.

Once the LDU and its external monitoring facility what is to be transmitted, the LDU assembles this data into transmission packets and preferably wirelessly transmits the packets 179. Transmission packets are typically from 64B to about 512B and include header data, optionally describing packet formatting and subject identity. As described, data transmitted can be general status 175, alarms including reason and severity 173, sensor data 171, and so forth. In addition to monitoring data, packets may also transmit monitoring system status (for example, battery charge, failure indications, and the like), position information, messages from a monitored subject, and similar data. If communication with external monitoring facilities are disrupted, the LDU preferably buffers data for retransmission.

Communication processing also regularly checks for incoming messages 181 from external monitoring facilities. Such messages include communication configuration commands (i.e., "I am your controlling monitoring subsystem") as previously described and requests and responses pertaining to data transmission. These messages also include values, trends, and alarms determined on the external monitoring facility and needed by the LDU, personalization data, system status information, messages from monitoring personnel, and the like.

External Monitoring Facility Processing/Communication Methods

External monitoring facilities receive data from dependent network elements, usually LDUs and other external monitoring facilities. They transmit selected received data to their controlling external monitoring facilities, usually the single principal external facility. An external monitoring facility cooperates with its dependent network elements to supplement their processing capabilities (if needed) and to select received data for transmission onward. A external facility (not the principal facility) cooperates with its controlling external facility to select data for transmission onward in a manner similar to cooperation between an LDU and its controlling external monitoring facility.

Figure 5:
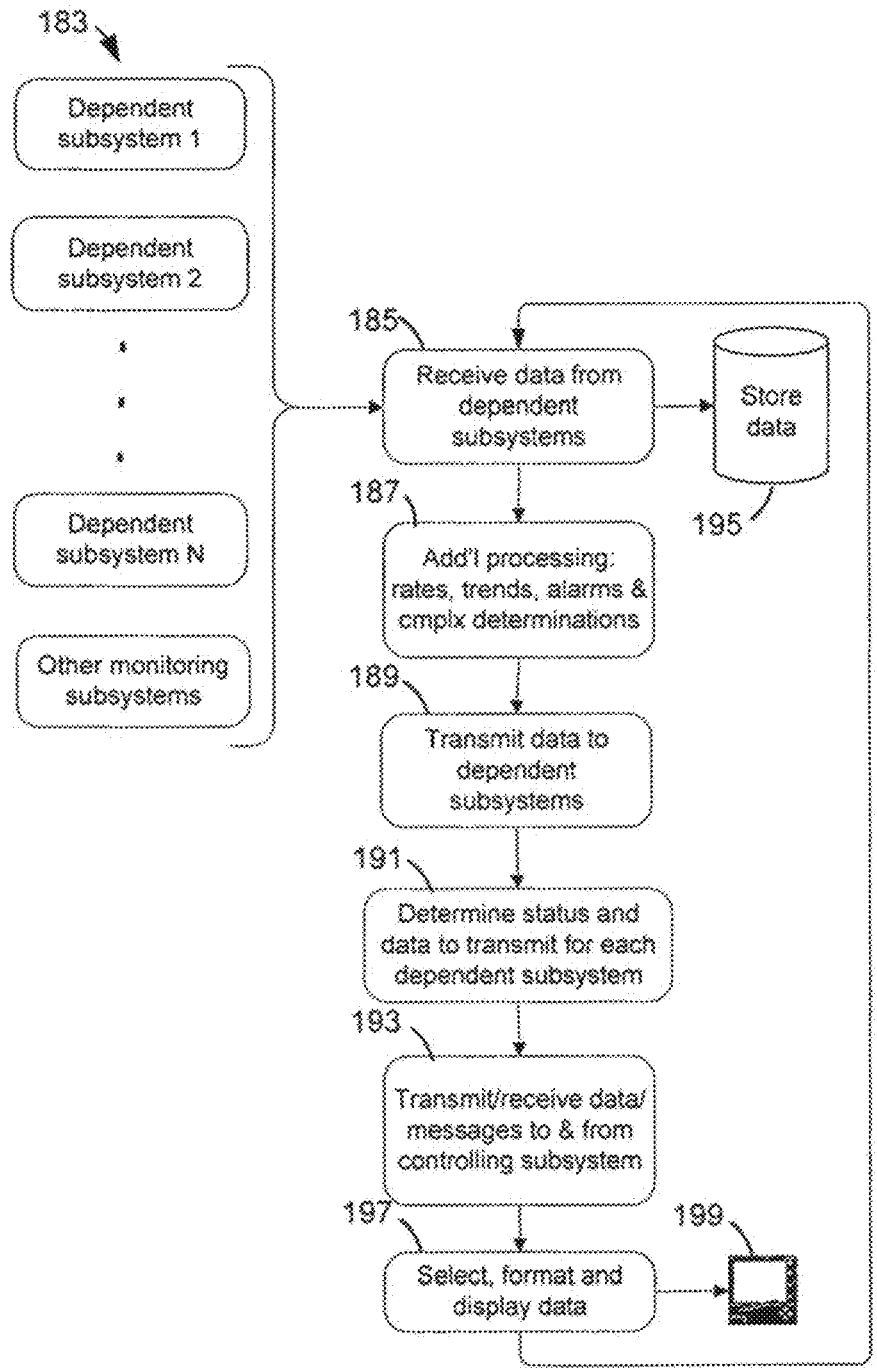
FIG. 5 illustrates processing external to the monitored subject.

FIG. 5 generally illustrates external monitoring facility data processing. Data and messages are received 185 from various other network elements 183 including one of more dependent LDUs and other external monitoring facilities. Two or more external facilities can also optionally form an ad-hoc-type network so that data can be forwarded from monitoring subsystems not in direct communication with a controlling external facility subsystem to an external facility that is in such contact. Optionally, some or all received data and messages can be locally stored 195 by the external facility. A single external monitoring facility can often receive different types of data (monitoring data of varying degrees of detail, system status messages, user messages, and the like) in heterogeneous formats from heterogeneous dependent subsystems. Accordingly, external facility preferably include formatting information so that all received data can be properly handled.

An external facility subsystem preferably performs sensor data processing and interpretation 187 that could not be performed on dependent LDUs (or on dependent external monitoring facilities), since such facilities often have greater processing capabilities. If sensor data is received, processing 187 can determine further physiological parameters and events, such as, respiration volumes as well as rates, respiratory events such as coughing, sneezing, cardiac stroke volumes and so forth, as well as cardiac rates, and further alarm conditions. See, for example, the "data processing and interpretation patents" and/or the "cardiac function patents" included herein. Results of such supplemental processing are transmitted 189 back to the LDU, or other dependent facility, from which the data came.

During step 191, an external monitoring facility cooperates with its dependent LDUs and external monitoring facilities to determine the status of monitored subjects and the data to be transmitted onward in the network. As described, the physiological status of a particular monitored subject principally determines the types and amounts of monitoring data that an LDU should transmit to its controlling external facilities, with worsening status generally necessitating increased data transmission. Thus, when an LDU detects a status change it requests its controlling external monitoring facility subsystem for permission to transmit additional data. The controlling facility may then grant permission for transmission of selected additional data. Alternatively, the external facility itself may detect status changes and may request the LDU to transmit selected data (optionally whether or not status has changed).

When an external monitoring facility has unused resources, it can request that all additional data be transmitted from a particular LDU. However, if the external facility has little or no unused resources, it is preferred that it select additional data for transmission from a particular LDU according to the severity of the stat of the subject monitored by that LDU. Generally, more comprehensive data is selected from subjects with more severe or dangerous status or in need of more immediate attentions; but less comprehensive data is selected from subjects with less severe status not in need immediate attention. In other words, as described, an external monitoring facility preferably perform "data triage" with respect to its dependent facilities in order that attending monitoring personnel are able to better perform medical triage.

Finally, a single external monitoring facility, perhaps having the greatest computational resources, can act as a principal external facility. The principal external facility controls all external monitoring facilities in the monitoring system with which it is in direct or indirect communication. Specifically, the principal external facility receives data concerning all subjects monitored by the monitoring system. It formats received data and presents it to monitoring personnel so that these personnel have a view of all monitored subjects and external facilities at selectable levels of detail. Also, it acts as an external monitoring facility for those LDUs in direct communication. It cooperates with those external facility in direct communication to receive subject status (preferably, also, status of facilities themselves) and to receive additional sensor data according to need and its available resources as already described for monitoring-subsystem-LDU cooperation. It can optionally provide message communications between monitoring personnel and monitored subjects.

Information Presentation

Both LDUs and external monitoring facilities present monitoring data from monitored subjects to monitoring personnel. Preferably, these presentations highlight physiologically significant data in readily appreciated formats using visual as well as audible or tactile modalities. Example preferred data presentations are described next.

FIG. 3A illustrates LDU display 91 for a monitored subject (for example, the subject A in FIG. 1A). Data window 93 presents individual data items for the subject grouped into summary alerts 99 and optional supporting parameters 101. Active alerts can be highlighted by color change, flashing, and the like, perhaps supplemented by audible or tactile warnings 97. Alerts are designed to compactly represent a serious or potentially dangerous physiological condition. Typically, such a condition is determined when a determined physiological parameter, or a combination of determined physiological parameters, are outside of a predetermined range. The particular data elements causing an alert can be indicated in supporting parameter area 101. Here, alert B, which reflects a physiological temperature out of range, is being signaled. Optional local status windows 95 may present the subject's location, the status of the monitoring equipment, messages to and from remote monitoring personnel, and the like. Not illustrated are optional user controls, such as input buttons. Alternatively, display 91 can be touch sensitive so that touching data or status areas selects and retrieves more detailed information.

The content of the local display reflects the display capability the LDU. For example, compact LDU 211 (FIG. 1B) may reasonably display, for example, only the presence of an alert and a selected local status, such as whether a message is pending. On the other hand, unit 223 (FIG. 1C) has a larger screen and more capable input for display of a larger number of data and status elements.

This invention also includes data presentations suitable for external monitoring facilities for several monitored subjects. Portable external monitoring facilities have LCD screens preferably of sufficient size to display status of several subjects, and external monitoring facilities not designed for portability, such as the principal external facilities, usually have one or more standard computer monitors. FIG. 3B illustrates an exemplary presentation format suitable for portable external facilities, such as portable external monitoring facility 223 (FIG. 1C) or portable external monitoring facility 49 (FIG. 2B).

Data window 103 displays the identities of the monitored subjects, and for each subject, data similar to, but preferably more detailed than, the data displayed in their LDU displays (such as that illustrated in FIG. 3A). One format is table 105 with rows (or columns) for monitored subjects and columns (or rows) with subject identification and their monitored data. Displayed monitored data preferably includes alerts, the physiological parameters leading to each alert, and optionally subject location. Row 109 shows that subject A has alert B caused by an out of range physiological temperature (corresponding in this case to the display on subject A's LDU in FIG. 3A). Optional local status windows 107 presents the monitoring subsystem's location, LDU status, communication status with other monitoring subsystems, messages to and from monitored subjects, and the like. Alert and warning conditions are optionally also indicated by audible alarms 111. Associated with this display are input equipment (not illustrated), such as buttons, touch sensitive screens, keyboards, pointing devices, or the like for entering commands and messages.

Figure 3C:
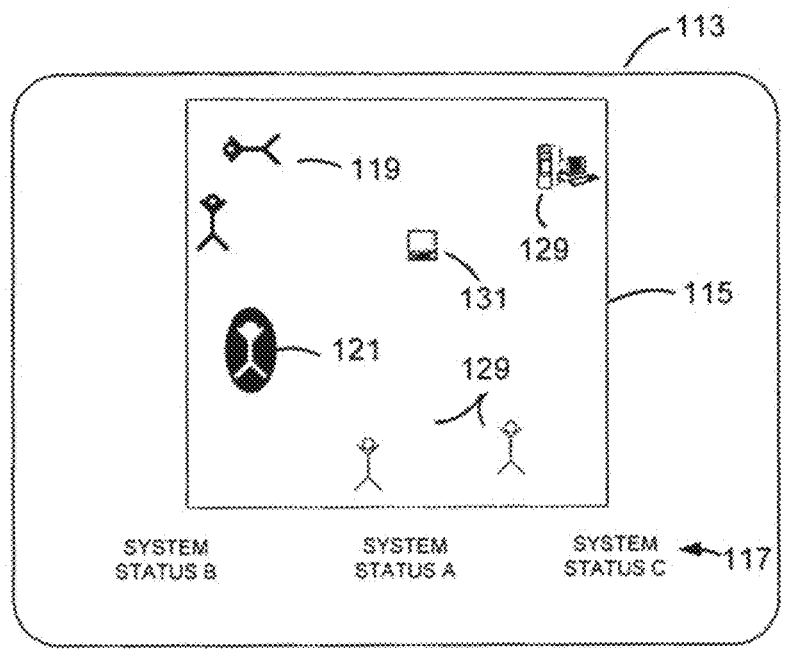
Figure 3D:
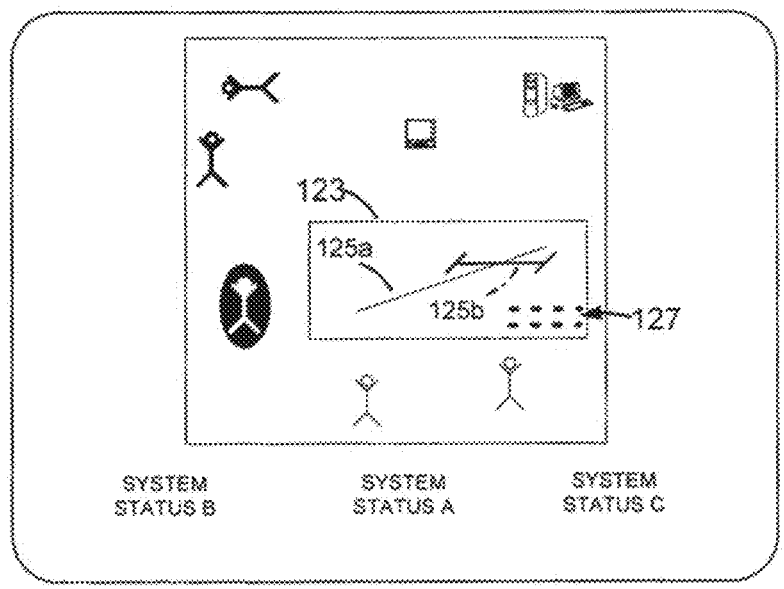

FIGS. 3C-E illustrate more preferable presentation 113 (especially when subject location information is available) suitable for external monitoring facilities with greater display capability, which are however often not portable. In these presentations, icons (optionally labeled or identified) represent system elements, that is monitored subjects and other monitoring subsystem data, are arranged in window 115 according to their relative geographical or spatial locations, which corresponds approximately to the arrangement illustrated in FIG. 2B. Status, alerts, and warnings pertaining to particular system elements are indicated by changes in their representing icons, such as highlighting, reverse background, flashing, color coding, labeling, and the like. For example, icon 119 represents that the corresponding monitored subject is recumbent (the other subjects are upright) but no alerts or warnings are indicated. On the other hand, icon 121 in reverse video indicates the corresponding monitored subject has a current alert condition, the particular alert preferably being indicated by color, texture, labeling, or other means. Further, the spatial display represented by window 115 can be scrolled, panned, zoomed, and the like as is known in the art, and can additionally by overlain by topography, building locations, environmental conditions such as temperature, and the like. This additional information may derive from stored map data and/or current environmental monitoring. System status windows 83, audible warnings, user input facilities, and so forth can also be provided. Here, one status window may indicate the status of system elements not currently being displayed in geographic window 115.

Preferably, selecting icon 121 subject to an alert (and also icons without alerts) causes display of relevant details on the alert condition (or other status). Here, selecting icon 121 causes display of exemplary detail-display-overlay window 123. This detail display shows trend line 125a for the subjects temperature exceeding safe threshold 125b. Also shown are optional alphanumeric data 127. These details allow remote monitoring personnel to conclude that this subject probably has an ongoing physiological problem. The subject may then be warned by a message directed to the LDU or emergency personnel may seek out this subject. In contrast, exemplary detail-display-overlay window 129 of FIG. 3E indicates a subject with an apparently transient physiological problem that has returned to normal. Temperature spike 131 could, for example, represent brief sustained activity that has now ceased (or could be an environmental artifact). The trends can preferably be scaled to display data for greater or lesser times and over greater or lesser parameter ranges. In further embodiments, trends for two or more related parameters, for example, heart rate and breath rate, can be overlapped in a single display window.

Preferably, personnel at any external monitoring facility with sufficient capability can request additional detailed data on a monitored subject. As described, pertinent additional detail data is preferably made available for subjects with not-OK status, and can be specifically required for all subjects.

Figure 3F:
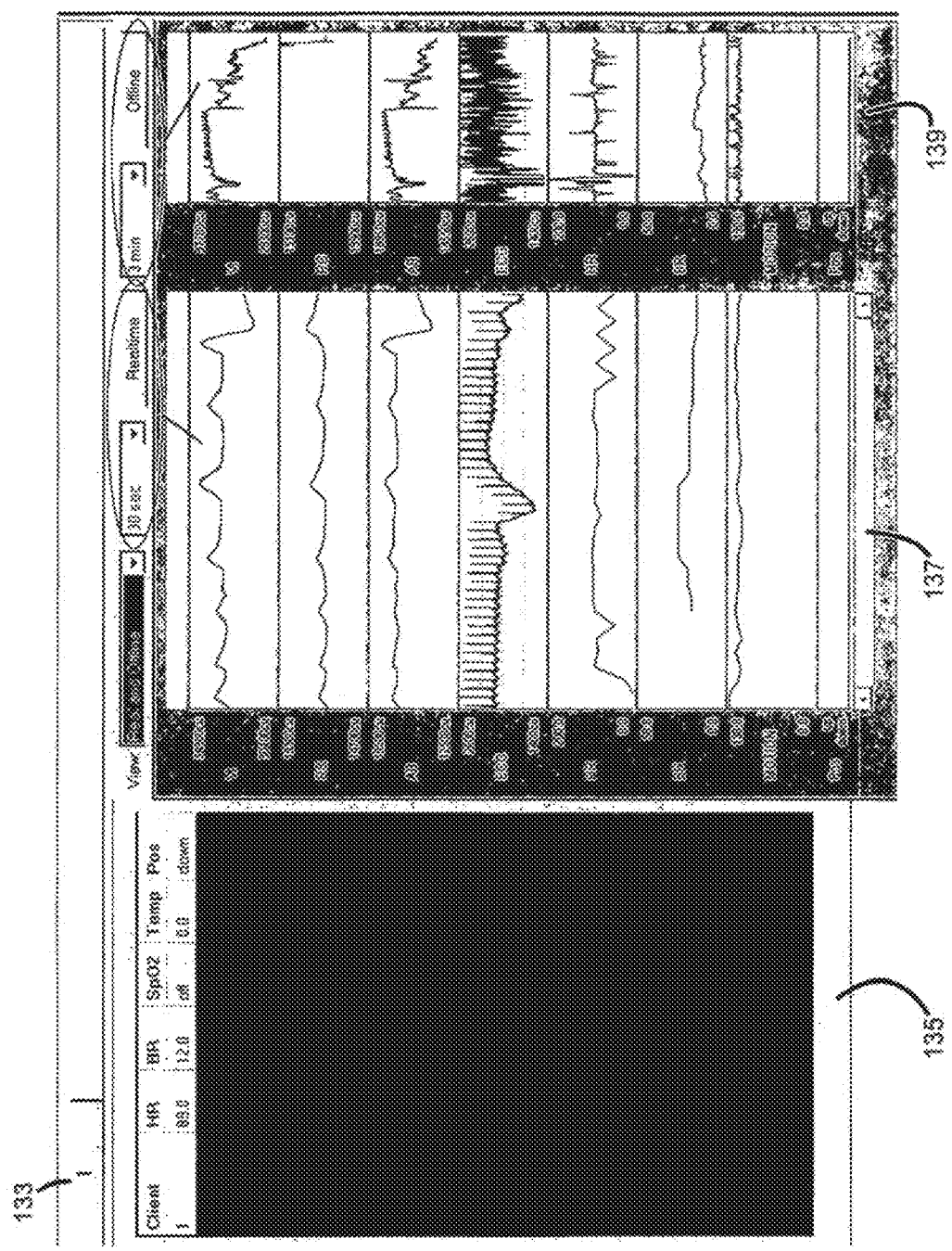

FIG. 3F illustrates an exemplary display of certain detail data. The display has been subdivided into three panels with summary data and two views of detailed sensor data. The summary panel 135 is formatted as a table similarly to FIG. 3B with data for each subject (here, a single subject) presented in a individual row of the table. Subject "one's" data is displayed: the heart rate is 89 beats per min.; the breath rate is 12 breaths per min.; the oxygen saturation data is not available; and the posture is recumbent. (A spurious temperature is set to trigger automatic transmission is presented in detail data.) Panels 137 and 139 present a real time view and an offline view of available detailed sensor data, which includes tidal volume (Vt), rib cage and abdominal expansions and contractions (RC and AB), ECG, heart rate (HR), breath rate (BR), activity indicia (MOTION), and posture (Pos). The real time view displays the past 30 sec of data as it is being collected. The offline view displays a selected 3 min. portion of past sensor data. Subjects can be selected for detail data display (if such data is available) by, e.g., selecting tab 133, selecting the subject summary lines, or other means known in the art. If sensor data is not being transmitted, commands to transmit requested sensor or other detailed data can be sent to the LDU.

In this manner, remote monitoring personnel may interact with the monitoring system of this invention to monitor subjects in potential physiological distress, determine and triage indicated distress, and take corrective actions.

5.2.3 Further Parameter Combinations and Alarm Conditions

Described herein are additional combinations of physiological parameters and associated alarm conditions. These combinations and conditions generally require increased processing. In embodiments where the LDUs have sufficient processing resources, it is preferred for the LDUs to determine these combinations and conditions and to forward results to external monitoring facilities. Where the LDUs do not have sufficient resources and where communication bandwidth permits, less processed data can be forwarded to the external monitoring facilities, which then make these additional determinations and return the results to the LDUs.

These additional combinations include at least ventilatory thresholds and indices of heat stress. Since real-time measures of monitored subject work, or effort, or energy consumption are advantageous inputs to these additional combination, such energy consumption measures are described next, followed by description of these additional combinations.

Measures of Energy Consumption

For the following reasons, this invention preferably senses raw data, in most embodiments, acceleration data, and processes this data into measures that correlate with subject energy consumption. First, it is advantageous to parameterize a subject's observed physiological responses with the subject's energy consumption, because metabolic responses, cardio-respiratory responses, and many general physiological responses correlate well with total energy consumption. Thus it can be determined whether observed physiological responses are expected given current energy consumption, or are anomalous for current energy consumption. The latter case may indicate physiological dys-regulation and warn of stress or impending danger. However, subject energy consumption is most accurately estimated by a subject's oxygen consumption (or carbon dioxide generation), a measurement that is too cumbersome for use in situations of potential physiological stress or danger.

Thus, since work done during activity is important in objectively assessing physiological responses in many situations, readily obtained measures that correlate with subject energy consumption are consequently desirable. Such correlative measures often include accelerometer data. A simple and direct measure is based only on accelerometer data, which can often alone provide information on increased energy consumption during activity because energy consumption usually reflects subject activity and subject activity often leads to accelerations. Such a measure is determined by regressing independently measured energy consumption against an acceleration measure such as total power in the accelerometer signals.

However, any single correlation of increased energy consumption with accelerations cannot be equally strong in all cases because similar energy consumption can produce different accelerations in different types of activity. For example, a subject may be pushing a heavy object, in which case considerable energy may be consumed with less significant acceleration. On the other hand, the subject may be walking or running, in which case the resulting accelerations can closely correlate with increased energy consumption. Also, varying biomechanical and metabolic efficiencies can alter the relation of energy consumption and acceleration. Thus a more advantageous measure of energy consumption is determined by regression of independently measured energy consumption against both accelerometer data and type of activity. Type of activity can be automatically estimated from accelerometer signal patterns as described below;

A preferred such measure is based on a combination of accelerometer data and activity type along with other physiological parameters returned from the monitoring apparatus. Desirable physiological parameters reflect cardiac outputs, e.g., heart rate and also stroke volume if available, and/or respiratory outputs, e.g., minute volume which can be readily estimated from respiratory rate and tidal volume. Also desirable are temperature, especially core temperature but also surface temperature compared to environmental conditions. The energy consumption measure is then found from regression equations determined by multi-variate regression of the accelerometer and other parameters against independently measured energy consumption.

Energy Consumption During Ambulation

Thus, the present invention includes at least one, and preferably a plurality of correlations of subject energy consumption with three-dimensional subject accelerations (known as tri-axial accelerometry), each correlation being adapted to a particular type of activity. One important subject activity is ambulation, for example, walking, running, and the like. FIGS. 6A-B each present four temporally simultaneous traces of raw and processed accelerometer data from an ambulatory subject. In each of the traces, time increases along the horizontal axis, while along the vertical axis: the traces labeled AccX record raw horizontal acceleration signals; the traces labeled AccY record raw vertical acceleration signals; the traces labeled AccM record total power (proportional to amplitude squared) in all acceleration signals; and the traces labeled Step record the occurrences of detected steps. Specifically, FIG. 6A illustrates data spanning an approximately one half minute period of walking; and FIG. 6B illustrates data spanning an approximately 15 minute period of mixed walking and resting.

FIG. 6A, especially, illustrates that ambulation, here walking, results in a clear pattern of vertical acceleration signals, primarily a sequence of relatively high amplitude, biphasic pulses occurring at constant or slowly varying overall frequency (the gait). The structure of these pulses reflect the foot contacting (actually to some extent bouncing on) a surface during ambulation. The pulse frequency and patterns of short pulse groups indicate the rate and character of ambulation, for example, discriminating walking, from running from skipping, and similar. Pulse amplitude indicates the intensity with which the foot contacts the surface, and when combined with pulse pattern, helps discriminate and confirm the type of ambulation. For example, a period of running has higher amplitude foot contacts than adjacent periods of walking.

The presence of foot contact pulses and pulse patterns indicative of ambulation, its type, and its intensity can be recognized in vertical acceleration signals by known signal processing methods. For example, step occurrences indicated in the Step trace were determined when the acceleration amplitude exceed a selected threshold factor (for example, a factor of 2) times a running mean of vertical acceleration intensity. Step frequency was determined as a declining running average of time between step occurrences, and step intensity was determined as the signal amplitude (preferably normalized in units of the acceleration of gravity (g)) when a step was recognized. Alternatively, the vertical acceleration signal can be wavelet filtered and decomposed at multiple resolutions. Step occurrences are then recognized from high resolution bands of the multi-resolution decomposition, and step amplitudes from the amplitude of coefficients in these bands. Gait frequency appears in the decomposition at mid-resolution.

FIG. 6B illustrates a longer duration during which periods of ambulation can be clearly distinguished from periods of rest (other stationary activities). The amplitudes of the vertical acceleration trace indicate the type of ambulation in the particular periods. Periods 211a and 211b are more quiet walking; periods 231a and 213b are normal walking; and during period 215 the subject was walking intensely or running.

Correlation between subject energy consumption and particular parameters describing acceleration signals are made by simultaneous measurement of acceleration signals and directly-measured energy consumption measurements during various types and intensities of ambulation. Such correlation may be determined across a population of physiologically similar individuals, but more preferably and more accurately are determined for each individual subject (thereby taking into account individual habitus, performance, training, and so forth). Necessary measurements can be partially automated by having the system instruct monitored subjects through messages presented at the subjects' LDU. For example, the system (by means of a program running in the LDU or on an external monitoring facility) can instruct a subject to walk and/or to run, and/or to perform other ambulatory patterns at a range of intensity levels. Relative amplitudes of concurrently measured acceleration signals can reveal the subject's apparent compliance. Alternatively and more simply, instead of being instructed by the system, a monitored subject may enter current activity type by means of user input functions on an LDU, perhaps by selecting from a menu of expected activity types.

A more preferred measure is determined by incorporating accelerometry data with measures including, but not limited to, heart-rate, change in heart rate, respiratory rate and volume, change in respiratory rate and volume, and other measures and derived values from the monitoring apparatus. All monitored data are analyzed by multivariate-linear regression to determine the dependence of the directly-measured energy consumption on type of ambulation (a discrete variable), characteristics of ambulation, such as step rate and intensity parameters (continuous variables) extracted from the accelerometer signals, and other physiologic measures determined to be relevant. The output is a single set of correlation coefficients relating monitoring data to energy consumption. Alternatively, first, without reference to energy consumption measurements, regression or clustering can associate accelerometer signal parameters with the type of ambulation. Then correlation of directly-measured energy consumption with accelerometer signal parameters is performed separately for each type of ambulation (as independently determined accelerometer signal parameters). Here, the output is multiple sets of correlation coefficients relating accelerometer signals to energy consumption separately for the types of ambulation. For increased accuracy, parameters reflecting patterns of adjacent steps can also by input to the above regression analyses.

The measures of energy consumption compactly represented in correlations coefficients (and other data resulting) can then be readily determined from acceleration signals for further uses and combinations with other physiological parameters as are next described.

Energy Consumption During Other Activities

These described methods can be applied to determine accelerometer-data-energy-consumption correlation useful in the other activities relevant to applications of this invention. For example, in athletics application, although accelerometer-data-energy-consumption correlations useful for running are as illustrated above, such correlations useful for swimming are different. Because accelerations during swimming generally have lower amplitudes distributed among different frequency components, different parameters must be extracted from acceleration signals, and these different parameters have correlation coefficients different from those for running. Generally, therefore, appropriate accelerometer signal parameters are extracted from signal power in different frequency bands, for example, determined using bandpass filters or multi-resolution wavelet decompositions, and so forth. These signal parameters are then used in a regression analysis to select significant parameters and their coefficients. For increased accuracy, signal correlations can be included in the regression.

An alternative approach uses a single parameter of total acceleration as a single regression parameter. For example, total power in all acceleration signals, the AccM traces of FIGS. 6A-B, can function as such a single parameter. For ambulation, FIG. 6A, and especially FIG. 6B, illustrates that the AccM traces correlates with the step amplitudes as indicated in the AccY traces, and therefore also with energy consumption. This parameter alone can be used as an index, albeit less accurate, of ambulatory energy consumption, and can also be used to correlate with energy consumption in other types of activity.

Additionally and alternatively, correlations between accelerometer signals and cardio-respiratory parameters can also be established during various types of exercise. Then energy output may be estimated in normal situations from cardio-respiratory parameters alone.

Ventilatory Thresholds

It is known that each subject generally has an energy consumption threshold, such that if the subject performs physical effort with a resulting energy consumption exceeding this threshold, the subject's minute ventilation (also referred to herein simply as "ventilation" and usually measured in liters/minute) increases with energy consumption more rapidly that if the subject's energy consumption is less than this threshold. FIG. 7 schematically illustrates a hypothetical subject's ventilatory response to activities resulting in increasing energy consumption and the subject's ventilatory threshold (referred to herein as "Tvent"). In the ventilatory region indicated as hyperpnea, where the subject's energy consumption is less than the Tvent energy consumption, the subject's minute ventilation increases with the subject's energy consumption in a generally linear manner at a lower rate. On the other hand, in the ventilatory region indicated as hyperventilation, where the subject's energy consumption is greater than the Tvent energy consumption, the minute ventilation increases also in a generally linear manner but at a greater rate. The Tvent, characterized by a threshold energy consumption and threshold minute ventilation, is the transition region between the subject's lower-work-output ventilatory response and the subject's higher-work-output ventilatory response, that is the transition from hyperpnea to hyperventilation. It is illustrated here as the region enclosed in the dotted boundary, because it is more usually found as a zone of transition and not as a precise point.

Tvent is an important marker of physiological stress and energy consumption for at least the following reasons. First, a subject can generally perform at sub-threshold activity levels, where energy consumption and ventilation are less than Tvent, for extended periods of time. Sub-threshold activity is within a subjects exercise capacity. However, at supra-threshold activity levels, where energy consumption and ventilation are greater than Tvent, the subject is facing imminent fatigue. The ventilatory threshold marks the workload above which metabolic acidosis is imminent or present. Supra-threshold activity levels are beyond a subject's capacity and cannot be long sustained. Physiologically, it has been found that the Tvent is close to those activity levels where lactate, a metabolic marker of impending fatigue, begins to accumulate in the blood. Second, it has been found that Tvent is a more reliable marker of impending fatigue than other easily measured physiological parameters. Heart rate alone, for example, is not a reliable marker of activity level thresholds because it is affected by a number of factors other than current energy consumption. For example, it is known to affected by both current emotional states such as fear and anticipated stresses likely in the near future.

Accordingly, it is preferable that a subject's activity be monitored with respect to that subject's Tvent, and that alarms be generated if the current activity is supra-threshold (or supra-threshold for more than a certain time duration). In one embodiment, this monitoring is done be ascertaining the subject's minute ventilation as the product of respiratory rate and tidal volume. Both these parameters can be extracted from signals reflective of the subject's rib cage cross section or circumference alone, and more preferably from the subject's rib cage and abdominal cross sections or circumferences (or equivalent measurements from which rib cage and abdominal volume changes can be determined) according to methods described in the "data processing and interpretation patents" previously included by reference herein. Such signals are readily sensed by, for example, the monitoring apparatus of FIGS. 1A and 1C, and also the monitoring apparatus of FIG. 1B. Additionally, a calibration procedure can be performed that allows subjects to gain feedback on the percent of ventilatory threshold at which they are working. This feedback enables the working individual to maximize their long-term work output.

In another embodiment, this monitoring is done by ascertaining the subject's energy consumption, which can determined as described above from accelerometer signals that correlate to energy consumption in known or determinable activities.

If both minute ventilation and energy consumption are available, they can both be used to confirm the subject's activity with respect to the subject's Tvent. If these two measures are inconsistent with past subject performance, represented for example by the correlations illustrated in an exemplary manner by FIG. 7 (or do not lie within expected uncertainties about past performance), it is preferable to indicate a further alarm or an increased urgency of an existing alarm. For example, if minute ventilation exceeds what is expected for the observed energy consumption, it is possible that the subject has already dangerously fatigued.

Determination of Tvent generally requires calibration for each individual subject, and preferably periodically recalibration because this threshold changes with the subject's fitness and health. Calibration can be done by instructing a subject to perform a series of activities with known energy consumptions spanning the range of the subject's exercise capabilities. Energy consumption can be measured directly, as, for example, by oxygen consumption or carbon dioxide production, or indirectly, as by accelerometer signals calibrated to energy consumption as previously described. In certain embodiments, external monitoring facility and/or LDU software can assist or control calibration by presenting a series of activity instructions to a subject and by measuring and determining the resulting minute ventilation and energy consumption in real time. Further, the software can check that the range of the subject's exercise capabilities have been spanned by the instructed activities. Resulting data can be analyzed to determined Tvent (the ventilatory threshold) by, for example, linear regression that fits minute ventilation over energy consumption. Thereby, hyperpneic and hyperventilatory performance regions can be found, and then their intersection at Tvent. See, for example, Thompson et al., *Comparison of Ventilatory Threshold Measurements Made by Ambulatory Plethysmography and a Mass Flow Device*, www.vivometrics.com/site/res_abstracts.html (last visited Jun. 10, 2004).

Real-time Tvent monitoring has further application in training programs, that is, structured plans that over time increase exercise capacity, in athletics and other endeavors. Because Tvent represents a subject's greatest sustainable exercise capacity, coaches, athletes, and others have used this parameter to design training program that distribute training time across sub-threshold, threshold, and supra-threshold intensities and then monitor the intensity of individual training sessions. Real-time monitoring of minute ventilation (and optionally energy consumption) during a training session can confirm that the subject is exercising at the correct level; and periodically recalibrating Tvent over a training program can reveal how and how fast the trainee's Tvent and exercise capacity is improving. Thus, the real-time feedback provided for the first time by this invention (to the best of the inventor's knowledge and belief) is quite valuable for the subject during training and their coach. Additionally, incorporating real-time heart rate feedback can increase precision in monitoring the subject's physiologic response to work and their physiological adaptation during a training program.

Indices of Heat Stress

Real-time energy consumption measures are additionally valuable in assessing possible heat stress and the like. It has already been described that, because many general physiological responses correlate well with the total energy consumption, it is advantageous to parameterize a subject's physiological responses with energy consumption. Further, parameterization over a range of energy consumptions then establishes normal response ranges so that anomalous physiological responses to current energy consumption become readily apparent. Anomalous responses may indicate physiological dys-regulation, stress, or even danger, and should be brought to the attention of the subject and subject's monitoring personnel. Tvent monitoring is one example: a subject cannot sustain minute ventilation and energy consumption above Tvent; observed minute ventilation is outside the observed range at the observed energy consumption may warn of dys-regulation.

Heat stress indices are another example. These indices reflect deviations of heart rate from the heart rate expected in view current activity as reflected in accelerometer signals (that correlate to activity and to energy consumption), and/or respiratory rate, and/or in minute ventilation. Heat stress indices, as is Tvent, are preferably calibrated and determined (and periodically recalibrated) for each individual subject as follows. First, expected heart rate is observed for a range of activity levels (determined from concurrently-measured accelerometer and/or respiratory), from lower sustainable activity levels to higher levels that are not sustainable (being above the Tvent). Second, the observed heart rate is correlated, for example, by linear regression, to the concurrently-measured accelerometer and/or respiratory data resulting in heat-stress correlation coefficients.

Then, during monitored activity, these heat stress index coefficients determine an expected heart rate from selected characteristics of concurrent accelerometer signals levels, breath rate, and/or minute ventilation that is compared to the actual, observed heart rate. If the actual heart rate is within expected bounds, the subject's condition is more likely to be normal or unexceptional. However, if the actual heart rate is outside expected bounds, the subject's condition is more likely to be non-normal or exceptional. In this cases alarms are preferably generated with a severity (for example, warning or danger) indicating the degree to which the actual heart rate diverges from the expected bounds.

Optionally skin temperature measurements can be included in the calibration and heat stress index regression coefficients determined for skin temperature. However, it has been found that skin temperature is often a late sign of stress. Skin temperature is thus not currently included in these indices. Further, from previous description, it will be remembered that the accelerometer-signal characteristics selected and their correlation with energy consumption vary with the type of activity. Certain activities, for example, walking, running, and the like, lead to distinctive accelerometer signals that correlate well with energy consumption, and therefore can make a have substantial contribution to heart stress indices. On the other hand, activities such as lifting, pushing, and the like, lead to weak accelerometer signals that correlate poorly with energy consumption, and make little contribution to heart stress indicia.

Additional Aspects and Embodiments of this Invention

Additional aspects and embodiments of this invention include an external monitoring facility for real-time monitoring of ambulatory subjects having a display; a communication interface for wireless communication; and a processing device operatively coupled to said display and to said communication interface that establishes communications with one or more portable monitoring apparatus, each portable monitoring apparatus monitoring an ambulatory subject and wirelessly transmitting physiological information concerning said subject, receives transmitted physiological information concerning one or more monitored subjects; and displays selected items of received physiological information.

This invention also includes the above external facility: wherein establishing communications further comprises requesting a portable monitoring apparatus to direct communications to said external monitoring facility; wherein establishing communications further comprises accepting communications from a portable monitoring apparatus that has selected said facility to receive communications from said portable monitoring apparatus; further having requesting a portable monitoring apparatus transmit items of physiological information that are selected in dependence on a physiological condition of said subject being monitoring; further having establishing communications with one or more other external monitoring facilities, each said other external monitoring facility wirelessly transmitting previously-received physiological information concerning monitored subjects; wherein transmitted physiological information concerning at least one monitored subject is selected in dependence on a physiological condition of that monitored subject; and wherein said displayed items comprise at least one icon representing a monitored subject;

This invention also includes the above external facility: wherein at least one of said icons has a displayed form selected in dependence, on and representing, a physiological condition of the monitored subject represented by the icon; wherein said displayed items comprise textual and/or numeric information concerning a monitored subject; wherein received physiological information concerning one or more monitored subjects comprises sensor data; and wherein said displayed items comprise said sensor data, wherein some or all said sensor data is displayed in graphical form; further having establishing communications with one or more other external monitoring facilities, and transmitting previously-received physiological information concerning monitored subjects, and optionally further having transmitting physiological information previously-received from one or more other external monitoring facilities.

Additional aspects and embodiments of this invention include: a system for real-time monitoring of ambulatory subjects having one or more portable monitoring apparatus as described above and one or more external monitoring facilities having a display, a communication interface for wireless communication, and a processing device operatively coupled to said display and to said communication interface that establishes communications with one or more portable monitoring apparatus, each portable monitoring apparatus monitoring an ambulatory subject and wirelessly transmitting physiological information concerning said subject, receives transmitted physiological information concerning one or more monitored subjects; and displays selected items of received physiological information.

This invention also includes the above system: wherein said portable monitoring apparatus wirelessly communicate with at least one of said external monitoring facilities, and wherein at least one external monitoring facility wirelessly communicates with at least one other external monitoring facility, and wherein said wireless communication comprises physiological information describing ambulatory subjects monitored by said portable monitoring apparatus; wherein one external monitoring unit is designated as a primary external monitoring unit, and wherein non-primary external monitoring units transmit to said primary external monitoring units previously-received physiological information concerning monitored subjects; and wherein said primary external monitoring unit is at least approximately 1000 meters or more from at least one of said portable monitoring apparatus.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A portable monitoring apparatus for real-time monitoring of an ambulatory subject, comprising:
    a wearable item comprising a sensor, the sensor providing a sensor signal responsive to the physiology of an ambulatory subject wearing the item; and
    a portable data unit local to the wearable item comprising a processing device configured to:
        retrieve and process the sensor signal in order to determine physiological information comprising an indication of whether a physiological state of the subject is normal or not or an indication of whether a physiological state of the subject is acceptable or not,
        present to the subject items selected from said physiological information, and to
        transmit items selected from the physiological information from the portable data unit to a remote monitoring station in dependence on the physiological state of the monitored subject,
    wherein the processing device is further configured to direct the transmission, wirelessly to the remote monitoring station, which is a current remote monitoring station selected from two or more candidate remote monitoring stations,
    wherein the processing device is further configured to select a new remote monitoring station from the candidate remote monitoring stations that is different from the current remote monitoring station; and is configured to direct future wireless transmissions to the new remote monitoring station and cease directing future wireless transmissions to the current remote monitoring station,
    wherein the candidate remote monitoring stations are assigned priorities, and wherein the new remote monitoring station currently has the greatest priority at portable data unit of the other candidate monitoring stations,
    wherein the physiological state is further determined by comparing a value of a physiological parameter to a predetermined threshold value that is acceptable or normal based on predetermined criteria.

2. The portable apparatus of claim 1 wherein, when the processing device determines that the physiological state is acceptable or normal, the processing device is further configured to transmit only an item representing an acceptable indication or normal indication.

3. The portable apparatus of claim 1 wherein, when the processing device determines that the physiological state is not acceptable or not normal, the processing device is further configured to transmit items, the items comprising sensor data or physiological information.

4. The portable apparatus of claim 1, wherein the remote monitoring station commands portable data unit to transmit selected items, and wherein the portable data unit transmits the selected items.

5. The portable apparatus of claim 1, wherein the remote monitoring stations transmit to the portable data unit, and wherein the new remote monitoring station currently has the greatest signal strength at the portable data unit of the candidate remote monitoring stations.

6. The portable apparatus of claim 1, wherein the selected items are encrypted prior to transmission.

7. The portable apparatus of claim 1, wherein the wearable item comprises one of a band, a shirt, and garment.

8. The portable apparatus of claim 1, wherein the wearable item comprises a band into which the portable data unit is incorporated.

9. The portable apparatus of claim 1, wherein the wearable item comprises a garment and a band attachable to the garment, and wherein the portable data unit is incorporated into the band.

10. The portable apparatus of claim 1, wherein the processing device is further configured to digitize signals from the sensor, wherein the sensor provides an analog signal.

11. The portable apparatus of claim 1, wherein the sensor comprises one of a cardiac sensor, respiratory sensor, accelerometer sensor, electrocardiogram sensor, electroencephalogram sensor, electro-oculogram sensor, electro-myogram sensor, surface temperature sensor, core temperature sensor, blood oxygen saturation sensor, sound sensor, ultrasound sensor, ballistic impact sensor, and electrical impedance sensor.

12. The portable apparatus of claim 1, wherein the sensor comprises one or more size sensors responsive to a size of the rib cage of the ambulatory subject or to a size of the abdomen of the ambulatory subject.

13. The portable apparatus of claim 12, wherein one or more of the size sensors is an inductive plethysmographic sensor.

14. The portable apparatus of claim 1, wherein the sensor comprises a posture sensor or an activity-level sensor.

15. The portable apparatus of claim 14, wherein the sensor comprises one or more accelerometers.

16. The portable apparatus of claim 1, wherein the physiological information further comprises one of a physiological parameter and a temporal trend of a physiological parameter, and wherein the physiological state is further determined in dependence on the determined physiological parameters or trend.

17. The portable apparatus of claim 16, wherein the physiological parameter further comprises one of a parameter describing a subject's lung function, a parameter describing a subject's cardiac function, a parameter describing a subject's posture, a parameter describing a subject's activity, a parameter describing a subject's temperature, a parameter describing a subject's ventilatory thresholds, a parameter describing a subject's energy consumption, and a parameter describing a subject's level of heat stress.

18. The portable apparatus of claim 1, wherein the processing device comprises one of a microprocessor and a field programmable gate array.

* * * * *